(12) United States Patent
Schultz et al.

(10) Patent No.: US 8,558,168 B2
(45) Date of Patent: Oct. 15, 2013

(54) POST-IONIZATION OF NEUTRALS FOR ION MOBILITY OTOFMS IDENTIFICATION OF MOLECULES AND ELEMENTS DESORBED FROM SURFACES

(71) Applicant: Ionwerks, Inc., Houston, TX (US)

(72) Inventors: J. Albert Schultz, Houston, TX (US);
Thomas F. Egan, Houston, TX (US);
Ernest K. Lewis, Pearland, TX (US);
Kelley L. Waters, Houston, TX (US)

(73) Assignee: Ionwerks, Inc., Houston, TX (US)

( * ) Notice: Subject to any disclaimer, the term of this patent is extended or adjusted under 35 U.S.C. 154(b) by 0 days.

(21) Appl. No.: 13/746,704

(22) Filed: Jan. 22, 2013

(65) Prior Publication Data
US 2013/0134305 A1    May 30, 2013

Related U.S. Application Data

(63) Continuation of application No. 12/692,604, filed on Jan. 23, 2010, now Pat. No. 8,384,023.

(60) Provisional application No. 61/146,890, filed on Jan. 23, 2009.

(51) Int. Cl.
*H01J 49/00*    (2006.01)

(52) U.S. Cl.
USPC .......................................................... 250/287

(58) Field of Classification Search
USPC .......................................................... 250/287
See application file for complete search history.

*Primary Examiner* — David Porta
*Assistant Examiner* — Hugh H Maupin
(74) *Attorney, Agent, or Firm* — Fulbright & Jaworski LLP

(57) ABSTRACT

The present invention relates to a method and apparatus for ionizing a neutral MALDI desorption plume, and in particular, for efficiently measuring the ionized MALDI desorption plume when post-ionization techniques are combined with a medium pressure MALDI-IM-oTOFMS instrument. Additionally, the present disclosure provides a method and apparatus that simultaneously separates tissue-sample MALDI ions by IM-oTOFMS according to their chemical family. After separation, the MALDI ions are directly compared to the ions created by post-ionizing the co-desorbed neutral molecules with a second laser wherein the second laser is delayed by a few hundred microseconds. The present disclosure further provides novel approaches that enhance the analysis of ions, including the use of giant fullerene internal standards to enhance mass accuracy, and ultraviolet (UV) declustering lasers to generate intact peptides and proteins, either of which may be followed by VUV post-ionization which generates identifiable structural fragments.

21 Claims, 17 Drawing Sheets

POST-IONIZATION OF NEUTRALS FOR ION MOBILITY OTOFMS IDENTIFICATION OF MOLECULES AND ELEMENTS DESORBED FROM SURFACES

CROSS-REFERENCE TO RELATED APPLICATIONS

This application is a continuation of U.S. patent application Ser. No. 12/692,604, filed Jan. 23, 2010, which claims the benefit of U.S. Provisional Application Ser. No. 61/146,890, filed Jan. 23, 2009, the entire contents of both of which are hereby incorporated herein by reference.

TECHNICAL FIELD

The present invention relates generally to mass spectrometry and, in particular, the present disclosure provides a method and apparatus for ionizing and analyzing the neutral MALDI desorption plume, the information from which has been largely under utilized in the prior art. More specifically, the present provides a method and apparatus for efficiently measuring the ionized MALDI desorption plume when post-ionization (POSTI) techniques are combined with a medium pressure MALDI-ion mobility orthogonal time-of-flight mass spectrometry (MALDI-IM-oTOFMS) instrument.

BACKGROUND OF THE INVENTION

Matrix Assisted Laser Desorption/Ionization-Imaging Mass Spectrometry (MALDI-IMS) can support modern pathology by precisely identifying "biomarker" molecules, whose identity and location in a tissue sample indicate the existence and progression of a specific disease (Caprioli et al., 2008). However, three primary problems intervene. One such problem involves resolving isobaric ions which have the same mass-to-charge ratio (m/z), but different structures. This problem prevents hundreds of important biomolecules weighing less than 2 kDa from being uniquely identified by mass spectrometry alone. Another problem associated with analyzing biomarker molecules through MALDI-IMS is that tens of thousands of matrix molecules are required to desorb and ionize one molecule of bio-analyte which causes the applied matrix films to be thicker than the tissue slice to be analyzed (Dreisewerd, 2003). Another typical problem is that neutral molecules are desorbed almost exclusively which means that very few ions are directly produced by MALDI for analysis. Ultimately, these problems contribute to the practical mass spectrometry imaging signal being limited as the laser spot size decreases.

For example, the intracellular analysis of single cells by MALDI is not possible because of the aforementioned problems. In fact, presently, practical molecular analysis by MALDI of any surface smaller than 100 square microns is very difficult because (1) an excess of matrix is required to activate the available analyte, (2) overlapping spectral interferences are difficult to interpret by mass spectrometry alone, and (3) poor ionization efficiency limits sensitivity. All of these factors limit the analysis of a small surface to only the identification of the easily ionizable majority molecular components on the cell or tissue surface. Despite these problems, remarkable progress has been made in applying MALDI-IMS to real world issues (Caprioli et al., 2008). Moreover, unique instrumentation and analytical procedures have begun to appear over the last ten years to separately address each of the limitations of MALDI-IMS (Sinha et al., 2007).

Recently, combinations of either pulsed electrospray or MALDI with IM-oTOFMS have revived the use of ion mobility for bioanalysis by not only providing separation of conformers, but separation based on charge state as well. In the case of MALDI, the useful mass range can simultaneously encompass from low mass elements to 300 kDa mass biocomplexes.

In general, ion mobility (IM) is used to separate gas phase ions by forcing the ions to traverse an electrically biased cell filled with an inert gas such as helium. The electrical acceleration of an ion in the ion mobility cell is restricted by many low energy collisions with the helium atoms such that the average drift velocity with which that ion moves is proportional to its shape. For example, a molecule with sixty carbon atoms moves nearly twice as fast when it is in the spherical form of a "buckyball" compared to a nearly flat graphene sheet (Von Helden et al., 1993; and, Shvartsburg et al., 1999). Ion mobility became an extremely potent tool for sorting nearly isobaric gas phase cluster ion structures. This was first realized when it was first shown that the combination of a pulsed ion source at the entrance of the ion-mobility cell entrance and an orthogonal time of flight analyzer at the cell exit could uniquely determine both mass-to-charge ratio and ion mobility drift time for each and every ion from a sample.

The notoriously difficult MALDI analysis of small molecules in tissue has been tremendously assisted by MALDI-ion mobility orthogonal time-of-flight mass spectrometry, in particular, MALDI-IM-oTOFMS (Jackson et al., 2007). "Chemical noise" is the euphemism for the unavoidable, unresolved ion signal which hinders or prevents the interpretation of MALDI spectra at a mass-to-charge ratio of less than about 1000 Da. When MALDI-IM-oTOFMS is applied, this otherwise worthless spectral background is separated into useful familial trend lines rich with conformational information that becomes clear in displays of ion mobility drift time versus mass-to-charge ratio. These trend lines uniquely identify the presence of lipids, peptides, nucleotides, and small molecules (including matrix ions) in tissue.

As described herein, the present disclosure provides a method and apparatus for ionizing the largely ignored neutral MALDI desorption plume, and in particular, for efficiently measuring the ionized MALDI desorption plume when post-ionization (POSTI) techniques are combined with a medium pressure MALDI-Ion mobility orthogonal time-of-flight mass spectrometry (MALDI-IM-oTOFMS) instrument. Additionally, the present disclosure provides a method and apparatus that simultaneously separates tissue-sample MALDI ions by IM-oTOFMS according to their chemical family, and then directly compares these MALDI ions to the ions created by post-ionizing the co-desorbed neutral molecules with a second laser which is time-delayed, typically by a few hundred microseconds. Also, the present disclosure provides a method and apparatus for using post-ionization to identify intact molecules of cholesterol, lipids, peptides, proteins, and giant fullerenes that may be present on tissue surfaces, spatial imaging of post-ionized molecules (e.g. cholesterol) in brain tissue, and indentifying controllable photofragmentation for in-situ identification of proteins and peptides. The present disclosure further provides novel approaches that enhance the analysis of ions, including the use of giant fullerene internal standards to enhance mass accuracy, and ultraviolet (UV) declustering lasers to generate intact peptides and proteins, followed by vacuum ultraviolet (VUV) post-ionization which generates identifying structural fragments.

BRIEF SUMMARY OF THE INVENTION

The present invention is directed to a method and apparatus for ionizing the ions and neutral species present in the MALDI desorption plume. More specifically, the present provides a method and apparatus for efficiently measuring the ionized MALDI desorption plume when post-ionization (POSTI) techniques are combined with a medium pressure MALDI-ion mobility orthogonal time-of-flight mass spectrometry (MALDI-IM-oTOFMS) instrument.

In some embodiments the present invention provides an apparatus comprising an ion source for repetitively or continuously generating ions and neutrals; a post-ionization device fluidly coupled to the ion source to post-ionize or fragment at least a fraction of the ions and neutrals; an ion mobility cell capable of receiving the post-ionized ions; an ion extractor, fluidly coupled to the ion-mobility device capable of extracting the ions; a time-of-flight mass spectrometer fluidly coupled to and accepting the ions and fragment ions from the ion extractor, a position sensitive ion detector fluidly coupled to the time-of-flight mass spectrometer to detect the ions and fragment ions. Once a sample or analyte is desorbed, a desorption plume is created. This desorption plume contains a number of species that includes but is not limited to, ions, ionized fragments, elemental neutrals, and molecular neutrals. Post-ionization is the process by which the species present in the desorption plume are ionized and/or fragmented by another ionization source. In some embodiments, the apparatus further comprises a timing controller that is in electronic communication with the ion source and the ion extractor. The timing controller is capable of tracking and controlling the time of activation of the ion source. Also, the timing controller is capable of controlling the activation of the post-ionization device and the activation of the ion extractor according to a predetermined sequence. In certain embodiments, the apparatus further comprises a data processing unit for analyzing and presenting data. The data processing unit in electronic communication with the ion source. In particular embodiments, the data processing unit is in electronic communication with the ion extractor and the position sensitive ion detector.

The post-ionization device is any device that can be used to ionize a species. For example, the post-ionization device may be a UV post-ionization laser, a VUV post-ionization laser, an excimer post-ionization laser, an IR laser, and a tunable photon source. In certain embodiments, the post-ionization device is positioned to ionize species, including neutrals and ions, at a location between the ion source and the ion-mobility cell. In additional and alternate embodiments, the ion post-ionization device is positioned to fragment ions at a location between the ion source and the ion mobility cell.

In some embodiments the post-ionization device is positioned before the ion extractor and is a photo-fragmentation device. In other embodiments, timing controller is in electronic communication with the post-ionization device, and/or the data processing unit is in electronic communication with said post-ionization device. In particular embodiments, the apparatus further comprises a multiple pixel ion detector positioned within the mass spectrometer.

Also, the present invention provides a method for collecting mass spectrometric data from a sample. The method comprises the steps of desorbing a chemical species from said sample which produces a desorbed plume comprising a neutral species. In some embodiments, the method further comprises the step of post-ionizing the neutral species generated in the desorbing step thereby creating a post-ionized species. In additional embodiments, the method further comprises the steps of separating the post-ionized species in a drift tube by ion mobility; and, further separating the chemical species in a time-of-flight mass spectrometer.

In some embodiments, the method further comprises the step of adding a matrix to the sample. In specific examples, the matrix added is a material added using an inorganic cluster ion beam, a vapor deposition system, a desorption deposition source, and any combination thereof. In some embodiments, the step of desorbing a chemical species is performed with an energetic particle.

In particular embodiments, the step of desorbing a chemical species is performed by pulsing an ionization source. In specific examples, the source is a UV MALDI laser, an excimer laser, an IR laser, a cluster ion beam, and/or a tunable photon source. In specific embodiments, the post-ionization step is provided by at least one post-ionization source. In some embodiments, the post-ionization step is provided by two or more post-ionizations sources with a time delay between the pulsing of each post-ionization source. In some embodiments, the post-ionization source is a UV post-ionization laser, a VUV post-ionization laser, an excimer post-ionization laser, an IR post-ionization laser, a tunable photon source and any combination thereof.

In particular embodiments, the post-ionization source is pulsed with a time delay in relation to the pulsing of the source or ionization source of the desorbing step. In general embodiments, the sample is a tissue, a cell, a biological sample, a chemical sample or any combination thereof. In some embodiments, the sample comprises an analyte and a calibrant. In additional embodiments, the calibrant is an internal calibrant. In other embodiments, the calibrant is an external calibrant. In specific embodiments, the calibrant is a giant fullerene. In particular embodiments, the calibrant is a derivatized giant fullerene.

In some embodiments, the method further comprises the step of filling an extraction region simultaneously with analyte and calibrant. In additional embodiments, the step of filling an extraction region further comprising the step of varying the sample energy. In additional embodiments, the step of filling an extraction region further comprising the step of varying the extraction frequency as a function of ion-mobility drift time. In other embodiments, the method further comprising the step of extracting the analyte and calibrant. In yet another embodiment, the method further comprises the step of measuring the mass and time-of-flight of the calibrant and measuring the time-of-flight of the analyte. In additional embodiments, the method further comprises the steps of comparing the time-of-flight of the calibrant and the time-of-flight of the analyte and detecting any non-linearities observed in the comparing step. In specific embodiments, the method further comprises the steps of correcting for any non-linearities observed in the comparing step and determining the mass of the analyte by comparing the time-of-flight of the analyte with the time-of-flight with the calibrant.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
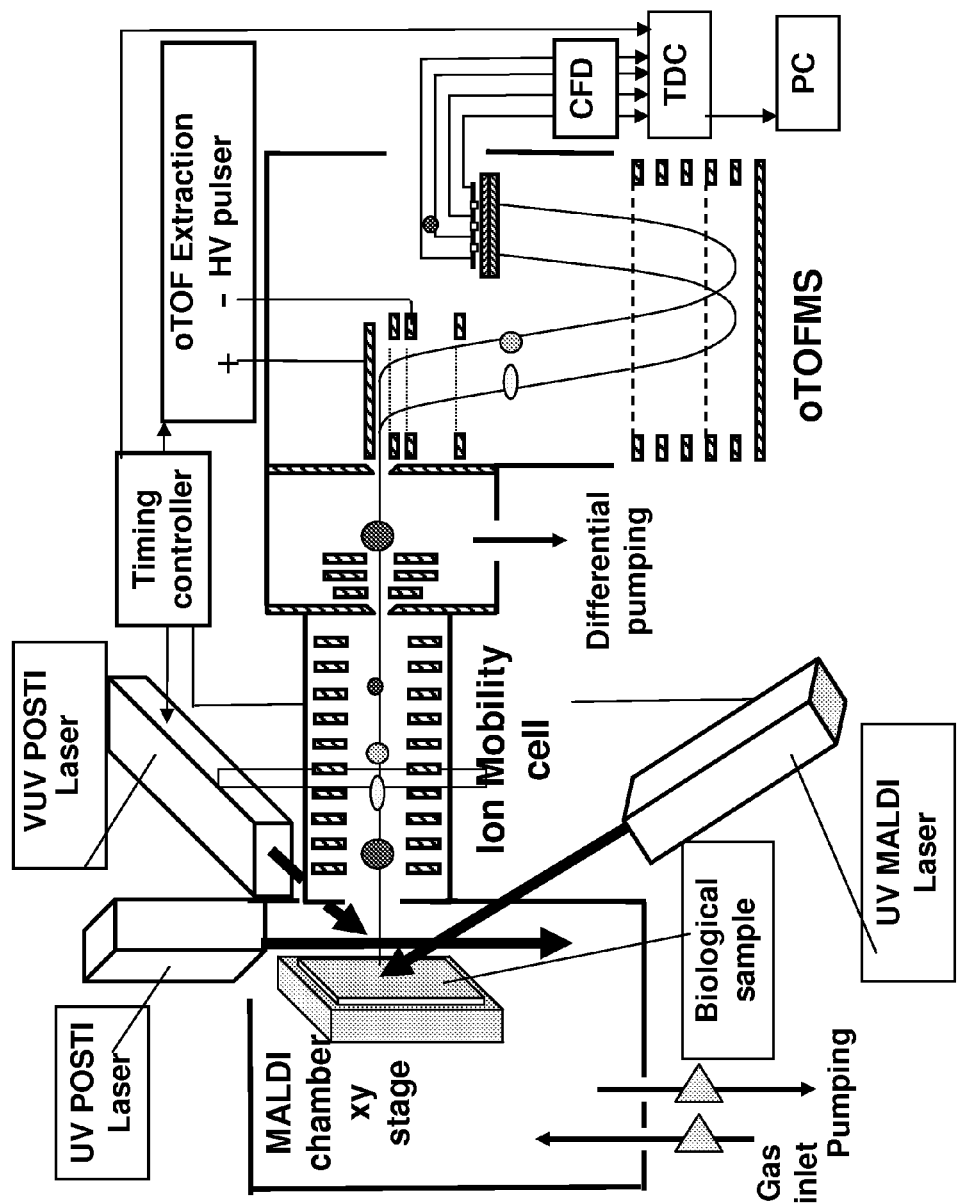
FIG. 1 shows a schematic of multi-laser microprobe post-ionization spectrometer which enables the simultaneous operation of direct MALDI followed by VUV post-ionization of the neutrals desorbed in MALDI.

Matrix addition to a tissue sample is problematic at best. The necessity of adding large molar amounts of organic matrix to desorb a small number of analyte molecules from a surface is substantially eased by the use of submonolayer coverages of nanoparticulates of carbon or gold (AuNP) as matrices. For example, pure Au400NP (1 nm diameter) nanoparticles (having 400 atoms) act as a highly efficient MALDI matrix. When Au400NP (1 nm diameter) particles are injected at submonolayer doses into the first 10 nm of a solid sample (e.g. pure protein film) or into the near surface region of a tissue sample, intact lipids, peptides and proteins are desorbed with an intensity that is superior to conventional organic matrices. Thus, gold and carbon nanoparticles allow the matrix to be a minority component of the sample by a ratio of 1:1000. This is the reverse of the typical MALDI experiment where 1000 organic matrix molecules activate one analyte molecule. A comparative study of these two approaches on rat brain tissue ion-mobility spectroscopy was performed using DHB (dihydroxybenzoic acid) or Au nanoparticulate (AuNP) matrices in a commercial MALDI-IM-oTOFMS. The results showed significant advantages of AuNP over DHB as an imaging matrix for lipids. Similar DHB derived images in an identical spectrometer have been achieved, and such studies have been extended to glioma tissue biopsies. MALDI-IM-oTOFMS may play a leading role in such studies, since this technique has the capability to record the mass-to-charge ratio (m/z) and ion mobility of any ion detected in the MALDI spectrum. The MALDI-IM-oTOFMS instruments is in contrast to differential ion mobility instruments which pass only one narrow region of ion mobility separated ions to the mass spectrometer.

The overarching requirement for a more powerful small area microprobe analysis of tissue is to develop a means to non-destructively ionize the thousands of neutral molecules desorbed and lost during one MALDI laser shot. It is necessary to begin with classic pump-probe experiments where ions and neutrals are co-desorbed (pumped) from a sample surface into a vacuum by a micro-focused laser pulse. Then, the resulting ions and neutrals are post-ionized (probed) a few hundred nanoseconds later by a VUV laser pulse aligned to cross and focus just above the surface into the rapidly departing neutral elemental and neutral molecular plume. For surface elemental analysis, sensitivities approaching the single-atom level are obtained by multi-photon ionization or VUV photo-ionization with a photon energy exceeding the ionization potential of the atoms. For example, elemental and isotopic composition of 1 μm dust particles from the crashed Stardust sample return mission have been successfully analyzed with a unique laser photo-ionization mass spectrometry technique at Argonne National Labs (Savina et al., 2003; and Veryovkin et al., 2005).

For molecular analysis, this elegant technique is sometimes very useful (Gaspar et al., 2008; and Edirisinghe et al., 2007). However more often, a VUV probe produces extensive and often useless molecular photofragmentation when neutrals are desorbed into a high vacuum where collisional cooling is minimal. Usually, the intact molecular ion is a small part of the signal compared to its fragments, and the intact molecular ion often disappears into the chemical noise.

Furthermore, because the neutral velocities are high in these experiments, the post-ionization must occur shortly after the MALDI laser is fired. This dictates a significant overlap between the MALDI and post-ionization signals. On the other hand, it is possible to produce a gas phase MALDI phenomena for molecular analysis by using a UV (or IR) probe laser to perform post-ionization of neutral analyte ions from within clusters of the matrix/analyte. Recently, other approaches, such as electrospray post-ionization, have been used (Vertes, 2007). As shown in FIG. 1, the present disclosure provides an apparatus comprising a pump-probe that uses different laser colors, coordinated timing sequences, and coupled to a pump-probe within the source region of our MALDI-IM-oTOFMS. In some examples the source region is helium-filled with a pressure of about 2.0 Torr.

FIG. 1 shows an MALDI-IM-oTOFMS spectrometer which contains an xy sample stage onto which is affixed a biological or other type of sample surface all of which is contained in a gas filled environment (helium in many cases) with a stable and controlled pressure suitable for performing laser desorption and Ion Mobility. An organic matrix (for example dihydroxybenzoic acid (DHB)) or a nanoparticulate (NP) matrix (for example AuNP) or combination of NP and organic acid may be added to the surface by solvent deposition or by thin film evaporation techniques to enhance the yield of molecular ions when a desorption source impinges the surface. A desorption source (e.g UV MALDI) impinges the surface to create directly desorbed ions as well as simultaneously co-desorbed neutral elements and molecules. An electrical bias is applied between the sample and the entrance to the ion mobility cell and continues along the cell. The ions which are directly desorbed from the surface by the desorption source (e.g UV MALDI) are extracted into the ion mobility cell (IM) and drift through the IM cell into the oTOFMS where they are extracted by a pulsed high voltage, accelerated towards and into and out of an ion reflector and finally their ion time of flight is measured by a multanode ion detector connected through a constant fraction timing discriminator (CFD) which inputs a timing pulse correlated with an ions arrival at the detector into a time to digital converter (TDC). The time between the application of oTOF extraction pulse and the arrival of the extracted IM selected ions at the multi-anode ion detector surface is measured by the TDC and recorded along with the ions' arrival times and also their drift times with respect to the application of the UVMALDI laser desorption pulse. Software can use calibrants of known mass and mobility to turn these arrival times into accurate representations of m/z and ion mobility drift times of unknown analyte molecules. After the directly desorbed ions have well entered the IM cell or the oTOFMS, the timing controller then provides a signal to control the firing of one of more post-ionization devices which specifically in FIG. 1 are non-limiting examples which include a UV POSTI laser and a VUV POSTI laser. Once a laser fires (for example the UV POSTI laser) then the neutrals which have desorbed in the initial MALDI event into a small volume a few millimeters above the sample surface are ionized by impinging the UV POSTI laser into this small volume. These "post-ionized" neutrals which have now become ions are then drifted by the electric field between the sample and the exit of the IM cell and their ion mobility drift times and m/z are recorded in the same way as was the IM and m/z of their directly desorb ion cousins. The ion mobility spectrometer in FIG. 1 also contains a second post-ionization source comprising post-ionization laser (e.g. VUV POSTI) which crosses above a sample surface in the helium-filled source region. The positioning of the post-ionization laser above the sample surface aids in the detection of the neutral molecules co-desorbed during MALDI both by declustering, by photofragmentation and by one photon photo-ionization. The schematic of the MALDI-IM-oTOFMS (Matrix Assisted Laser Desorption-Ion Mobilty-orthogonal Time of Flight Mass Spectrometer) shows a pulsed MALDI pump laser UV that simultaneously desorbs ions and neutrals into 2 Torr helium. In some examples, the MALDI pump laser is a UV or IR laser to name a few. In additional examples, the laser is pulsed or continuous. For the first few microseconds after the UV desorption pulse, the neutrals and ions leave the surface with similar velocities usually around a few hundred meters/sec although these velocities can vary over the range of 1 to 1000 m/sec depending on the fluence of the UV MALDI laser. However, after about 10 microseconds the neutrals have cooled into a volume of about 1 mm diameter through collisions with helium and have begun diffusing in all directions. The dimensions of the neutral desorption volumes have been confirmed through MonteCarlo simulations. Meanwhile, the MALDI ions are being drawn immediately into the ion mobility (IM) cell by an applied voltage between the sample and the entrance of the helium filled ion mobility cell. The ion mobility separation of MALDI ions of the same mass, but different surface areas will begin before the ionization of the stagnant neutrals. Small dense MALDI ions quickly traverse the ion mobility cell and enter the mass spectrometer where a rapidly applied pulsed voltage deflects the ion beam into a reflectron time-of-flight mass spectrometer followed some time later by larger or less dense MALDI ions. Ion drift times are typically under one millisecond for a mass-to-charge ratio of 5000. Yet, the time of flight in the mass spectrometer is typically only a few tens of microseconds. Thus, after each UV MALDI desorption pulse, several hundred mass spectra can be obtained as the ion mobility-separated MALDI ions elute into the oTOFMS. While this separation is in progress, the neutrals can be ionized by firing the VUV probe pulse 200 microseconds later (see FIG. 2). Thus, the co-desorbed neutrals which originate from precisely the same location on the surface can be measured simultaneously. This is quite a useful advance, since several tens of thousands of neutral molecules are liberated for every ion created by the UV MALDI probe pulse (Driesewerd, 2003). So, two IMMS spectra—one from direct desorption and one from post-ionization are recorded and appear offset by 200 microseconds (time between the pump and probe laser shots) as shown in the data from a rat spinal tissue section (FIG. 3). In each spectrum (MALDI and POSTI) the Ion Mobility separates lipids, neuropeptides, matrix molecules, and, if present, carbon or AuNP clusters. It is noted that there is an approximate 15% decrease in IM drift times between isobaric ions in each of these different groups (lipids are slowest and Au or carbon clusters are fastest).

Figure 2:
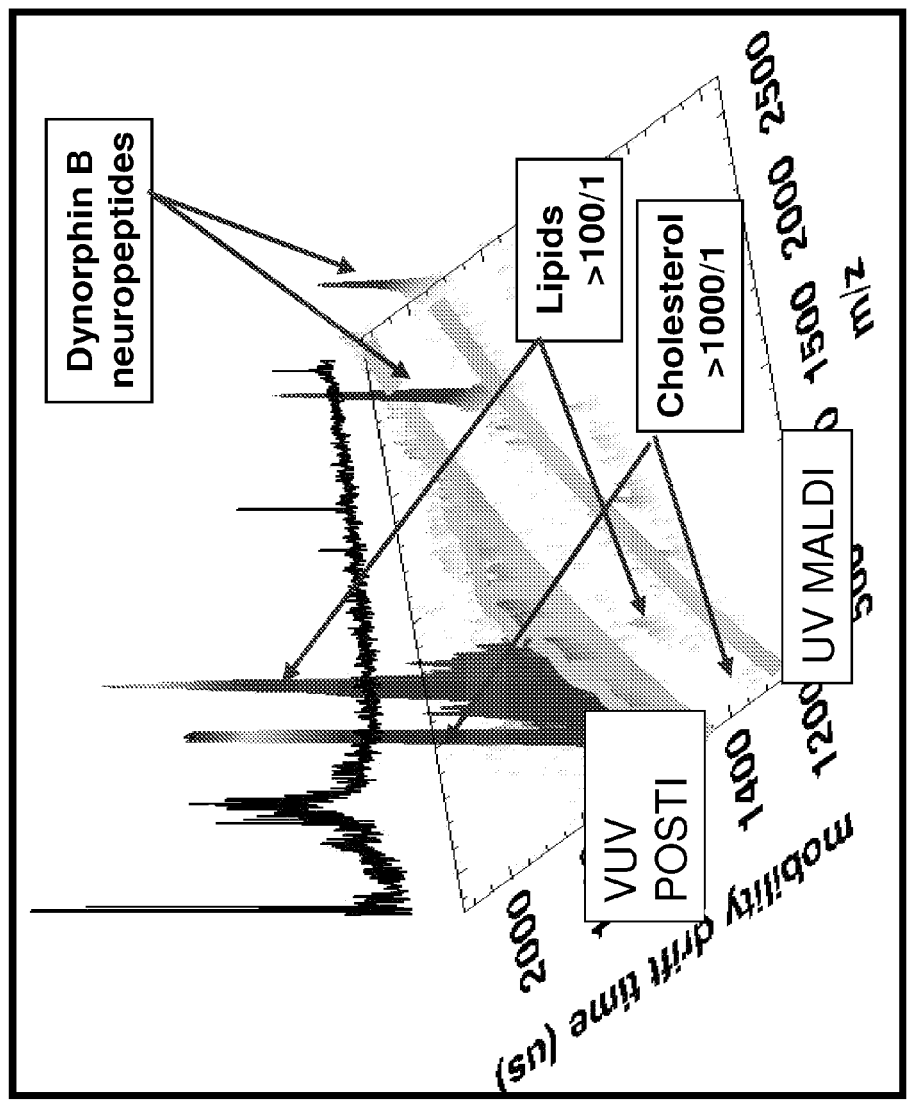
FIG. 2 shows data from a rat spinal tissue sample.
Figure 3:
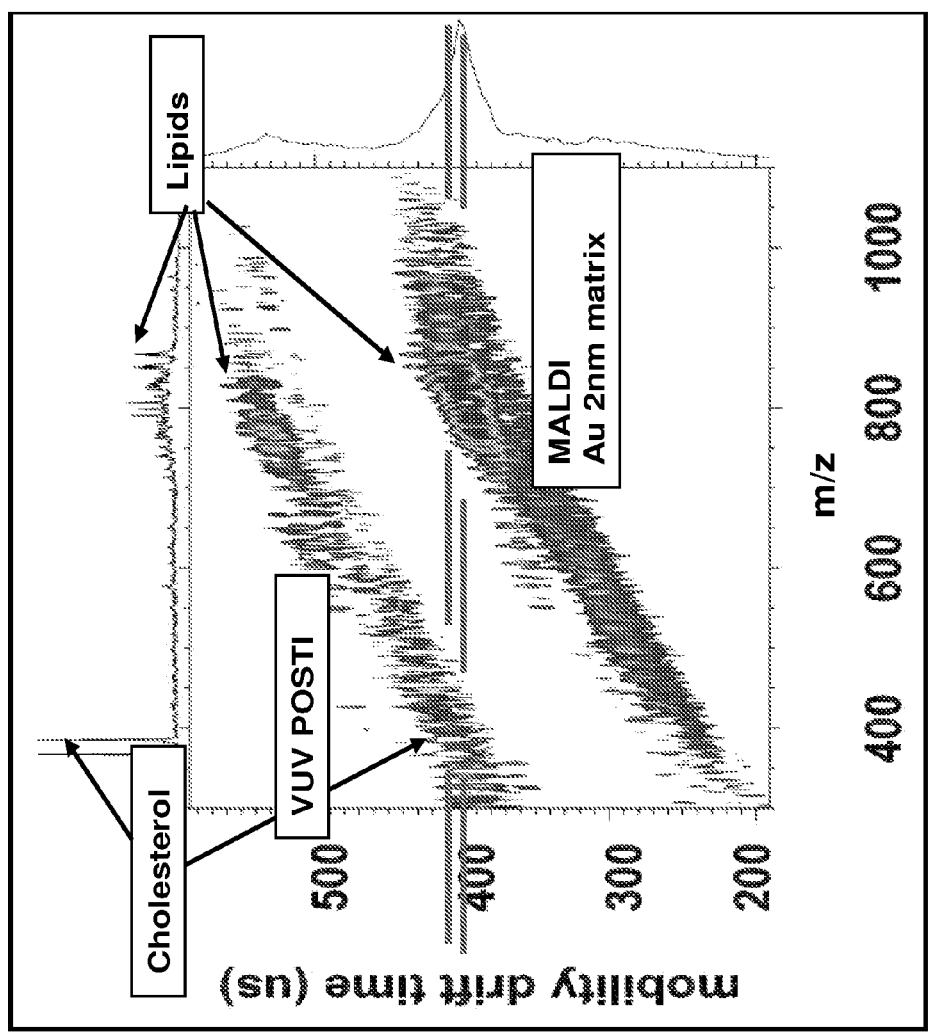
FIG. 3 shows an IM-oTOFMS spectrum of ion mobility drift time versus mass-to-charge ratio (m/z) obtained from a tissue with a 2 nm AuNP (gold nanoparticulate) matrix at coverages of 0.2 monolayer (or less) which enables VUV Post-ionization of neutral cholesterol and lipids desorbed during MALDI.

The post-ionization which is added to MALDI-IM-oTOFMS shown in FIG. 2 represents a significant advance, since several tens of thousands of neutral molecules are liberated for every ion created by the UV MALDI probe pulse (Driesewerd, 2003). Thus, two discrete IM-oTOFMS spectra recorded in the same experiment. One spectrum results from direct desorption and the other spectrum results from post-ionization. The two IM-oTOFMS spectra are offset by 200 microseconds which is the time between the pump (UV-MALDI) and probe (VUV-POSTI) laser shots. The two spectra shown in FIG. 2 were collected from a rat spinal tissue section covered with DHB matrix. The VUV-POSTI creates ions which are normally not seen in MALDI (such as the intact cholesterol radical cation).

In FIG. 2, the one dimensional mass spectrum (which is conventionally measured) is derived from the ion-mobility data and displayed at the top so that each mass-to-charge ratio irrespective of their ion mobility appears (summation of all MALDI and POSTI). However, the 3D contour plot shows the discrete spectra for MALDI and POSTI. The MALDI source pulse and the POSTI source pulse(s) are separated by a delay time with the POSTI laser pulse being delayed from 0.001 microsecond to 1000 microseconds relative to the MALDI laser. Within the MALDI and the POSTI spectra the lipids, peptides and matrix ions are resolved by the ion-mobility cell into familial trend lines.

In each spectrum (MALDI and POSTI), the ion mobility separates lipids, neuropeptides, matrix molecules, and if present, carbon or AuNP clusters. It is noted that there is an approximate 15% decrease in ion mobility drift times between isobaric ions in each of these different groups. Lipids are slowest and gold or carbon (and their clusters) have the fastest ion-mobility drift times for a given m/z.

The data in FIG. 2 was acquired in 60 seconds. This data shows the enhanced detection of lipids and cholesterol by POSTI in comparison to the detection of these species with MALDI techniques alone. In general, the POSTI lipid ions are more representative of the lipids known to be in the spinal cord. Over 57 major lipid peaks have been identified from the families Sphingomyelin (SM), Phosphotidyl Choline (PC), and most surprisingly of all Phosphotidyl Serine (PS), and Phosphotidyl Ethanolamine (PE) lipids. Additionally, there are 30 additional unassigned peaks that are seen in the mass-to-ratio and mobility region for Sulfatide, Cerebrosides, Phosphotidyl Inositol and Phoshotidyl Inositol Phosphate. The relative intensities of the different lipid families roughly mirror the known overall lipid concentrations in rat spinal extracts. In contrast to MALDI, the MALDI spectrum shows only six distinct lipid peaks from either SM or PC. Subsequent work with pure lipid standards indicates that all the lipid families, except Sulfatide, are remarkably stable to VUV irradiation. Even in the VUV irradiation of ST, only the sulphate is lost and the remaining cerebroside fragment carries the charge. Furthermore, despite the lipids provenance from salty tissue (attested by the preponderance of cation attached molecules in the MALDI), the VUV POSTI lipid spectra are almost completely devoid of cation attachments. Only the $MH^+$ lipid peak is present. Surprisingly, this holds true for PE and PS which are negative lipids and are almost never detected as a positive ions in MALDI. In POSTI, the PS and PE which are the most predominant of the lipid classes in the tissue. Also, the PS and PE are the most intense $MH^+$ POSTI signal. The relative intensities of all lipid $MH^+$ in POSTI reflect their known abundance in the tissue while in contrast, the MALDI shows only PC and PS. The cholesterol is predominant throughout the tissue and is barely detected in the MALDI spectrum, but is seen in the POSTI spectrum as two major groups of peaks. The two major groups of peaks are an intact radical cation which results from a hydrogen loss and a water loss fragment. Generally, post-ionization occurs within the ion-mobility cell. POSTI Microprobe images of lipids and photo-ionizable molecules are aided using this additional sensitivity technique (see FIG. 2 and FIG. 3).

In contrast to lipids, peptides are efficiently photocleaved by VUV at the amide bond. This cleavage at the amide bond occurs at least in high vacuum where there is minimal opportunity for collisional cooling. It has been shown that both peptides and proteins are easily photofragmented into predictable structural fragments in 2 Torr Helium. This is seen by comparing the MALDI and VUV POSTI in FIG. 2. In the MALDI spectrum of rat spinal tissue, the two dynorphin neuropeptides are prominent. In FIG. 2, the two dynorphin neuropeptides and their structural fragments are weakly present in the VUV POSTI. Thus, the VUV photofragmentation may be extremely useful for structural identification of unknown peptides when analyzing complex tissue samples. The presence of the peptides and proteins in the MALDI followed by analysis of their fragments produced by VUV can allow unambiguous identification of MALDI peptides even from tissue. The two important implications from FIG. 2 are: Ions are created in the VUV-POSTI are often never present in the UV MALDI, Secondly, UV-MALDI produces intact peptides, while VUV POSTI efficiently creates useful structural fragments from the co-desorbed neutral peptide fraction. These two-laser sequences can therefore be used for unambiguous in-situ structural identification within small areas of the biological tissue. Moreover, the post-ionization has applications where purified molecules have been located on a surface or onto a MALDI matrix surface. These applications may include surfaces such as the readouts of 2D gels, pull-down arrays, or other high throughput applications where laser desorption or MALDI is used to interrogate the spatial location of molecules or elements on a surface.

AuNP matrix (2 nm) at coverages of 0.2 monolayer enables VUV post-ionization of neutral cholesterol and lipids co-desorbed during MALDI (see FIG. 3).

In FIG. 3, MALDI-IM-oTOFMS and the firing of the VUV pulse were done with identical sequences to that in FIG. 2. However, in this case a brain tissue slice covered with sub-monolayer AuNP matrix is analyzed. As seen in FIG. 3, notice the intense production of cholesterol ions, as well as additional lipids which are not seen in MALDI. Unlike the result from DHB (FIG. 2) the POSTI and MALDI lipid signals from AuNP are seen here to be nearly equal in intensity. AuNP is inherently a more efficient MALDI matrix than DHB for certain lipids. Furthermore, if the VUV pulse is delayed by 800 microseconds extensive coverage of unassigned lipid peaks in the range 1000-2200 m/z are observed which are not seen nearly as well with DHB.

Figure 4:
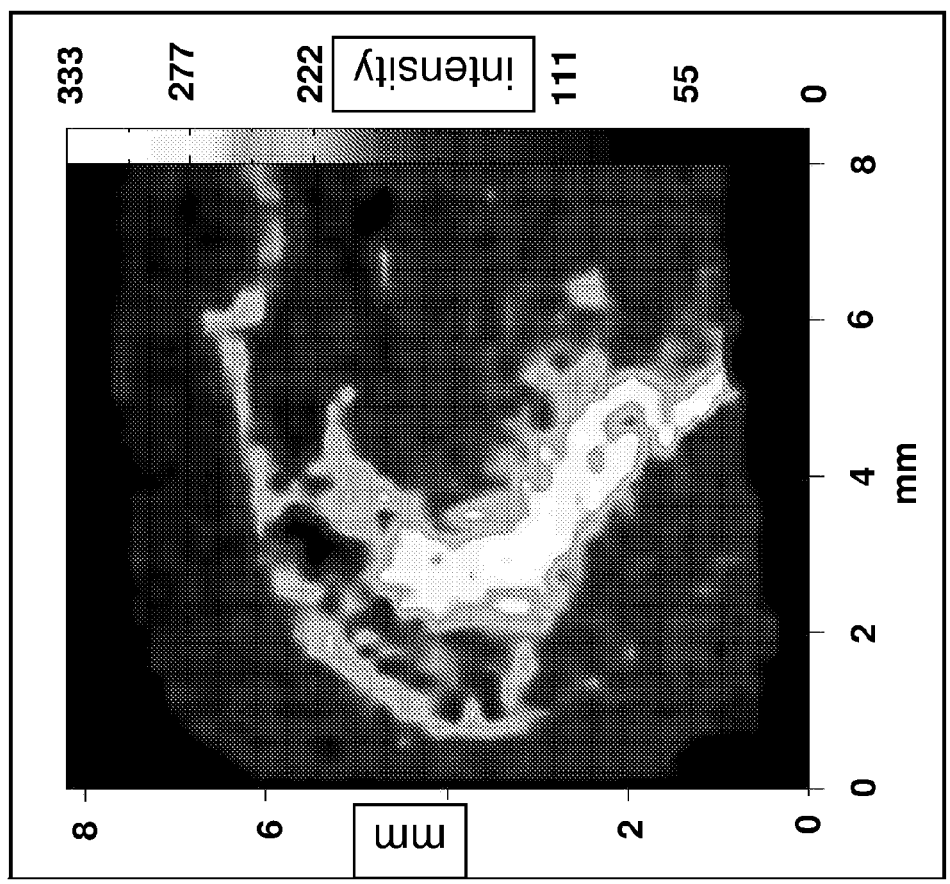
FIG. 4 shows a VUV-POSTI image of cholesterol from photoionized rat brain tissue sample covered with AuNP matrix. Pixel spatial resolution is less than 50×100 microns, and the entire image was acquired in less than three hours with maximum counts per pixel of 333 cholesterol ions.

FIG. 4 shows the first ever VUV rat brain tissue image using post-ionization. The cholesterol radical cation at m/z 386 (between the horizontal bars in FIG. 3) was produced by one photon photo-ionization by the fluorine laser. The ion intensity has been plotted as a function of the laser position on the tissue and the intensity of the cholesterol ion at each pixel is represented by a gray scale with white being most intense.

Microprobe imaging using the signal from photoionized cholesterol is shown in FIG. 4. Cholesterol is found in all cellular and organelle membranes, and makes up nearly half of membranes lipids. The relative intensities of the cholesterol and lipids are consistent with the known distribution of lipid and cholesterol as is the microprobe image of FIG. 4 which show cholesterol to be uniformly high in all locations with higher concentrations in certain regions.

Figure 5:
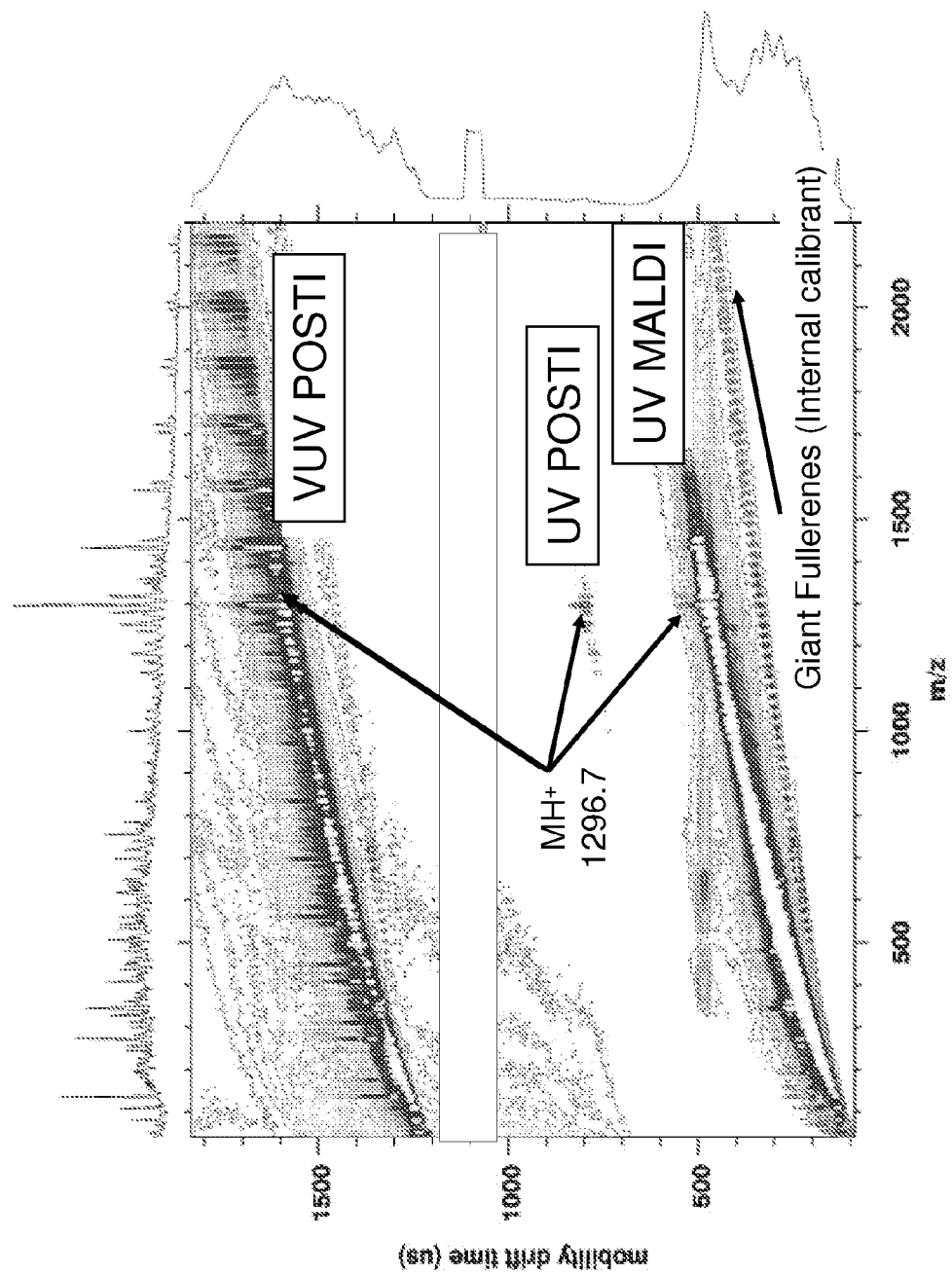
FIG. 5 shows a chart of ion mobility drift time versus mass-to-charge ratio wherein Angiotensin II (1 fmol deposited in DHB, no desalting) was loaded onto the sample plate.

In FIG. 5, three lasers (one for desorption and two for post-ionization) are fired in the following order: MALDI UV (349 nm) is pulsed, then 300 μsec later a second UV POSTI laser (349 nm) is pulsed into tightly focused volume located 0.2 mm above the surface, and finally 1.1 msec later the 157 nm VUV-POSTI pulse is also fired into the stagnant neutrals.

Figure 6:
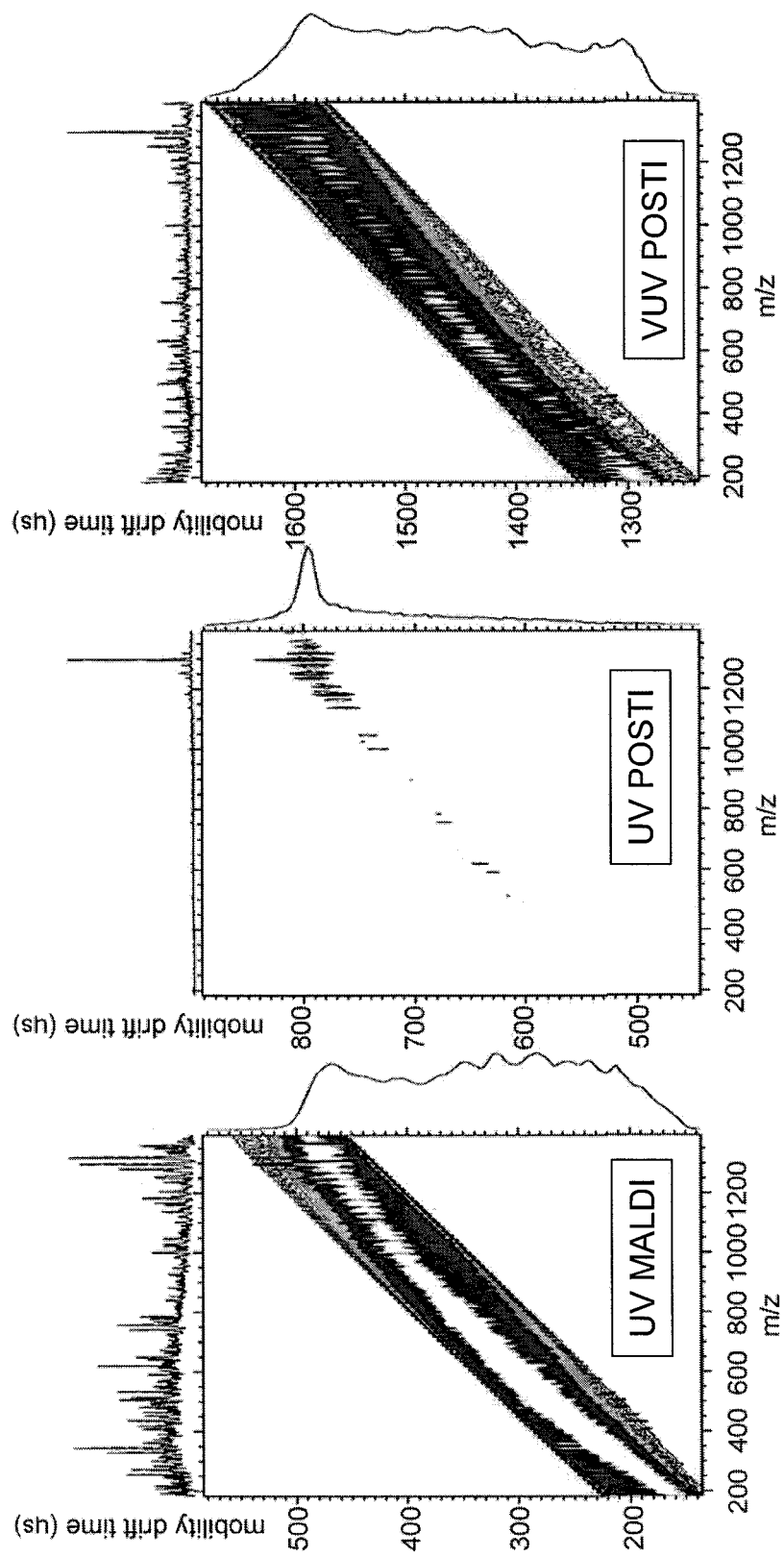
FIG. 6 shows a pure MALDI, UV and VUV post-ionization MS numerically abstracted from the data in FIG. 3A.

In some examples, peptides can be sequenced by the use of POSTI-IM-oTOFMS. As shown in FIG. 5 and FIG. 6, UV and VUV post-ionization provides complementary information on intact peptides and their fragments. While the VUV post-ionization is excellent for analyzing intact lipids and small photoionizable molecules like cholesterol, it is also extremely efficient for generating predictable structural fragment ions from peptides and proteins. By using a third laser for POSTI, unfragmented MH+ peptides are liberated from neutral matrix clusters that are co-desorbed from salty surfaces during MALDI. The third laser (UV POSTI) used has a 349 nm wavelength which is identical to the MALDI laser. The capability to desorb ions with the UV MADLI, to then create largely unfragmented gas phase molecules using (UV-POSTI) and finally creating fragments from a portion of these UV-POSTI ions by applying VUV-POSTI is demonstrated first in the test peptide angiotensin and will then be extended to a tissue sample in later examples. We sequentially applied three lasers (1) a UV MALDI laser (349 nm) for MALDI microprobe desorption, (2) a UV POSTI laser (349 nm) for the post-ionization of neutral peptides and lipids, and (3) a VUV-POSTI laser (157 nm) for post-ionization (which creates intact lipids and cholesterol) and predictably photo-fragments large peptides into smaller structural ions. Thus on the same sample spot multiple information can be sequentially obtained from each MALDI laser desorption event so that the parent ion mass is created and measured (both by UV MALDI and UV POSTI) and the structural sequence fragment of these intact peptides and proteins is provided by VUV POSTI from the same spot on a surface. There is a particular sequence for acquiring the data. First, a UV MALDI laser pulse of 349 nm is fired on to the sample. Then after a 300 µs delay, a second 349 nm laser (UV POSTI) is focused and fired into a 100 cubic micron volume at an elevation of 0.3 mm above the surface. The VUV POSTI laser is fired 800 microseconds after the second sequence. The importance of the data in FIG. 5 and FIG. 6 is that the UV post-ionization laser non-destructively dissociates and ionizes angiotensin/matrix gas phase clusters. Notice the remarkable reduction of in-source decay fragmentation from the UV POSTI (middle panel of FIG. 6) in comparison to either the MALDI spectra or to the VUV POSTI spectra of FIG. 6.

The major conclusion from FIG. 5 and FIG. 6 is that UV post-ionization (middle panel of FIG. 6 UV-POSTI) produces almost exclusively MH+ and very few structural fragments. Thus, a user can program multiple laser sequences to create a variety of desirable information from the neutral plume. For example as shown in FIG. 5 and FIG. 6, the neutral intact angiotensin is desorbed during MALDI first by UV post-ionization (gas phase MALDI) and thereafter by VUV POSTI. The VUV POSTI declusters, ionizes and photofragments the peptides. It is estimated that the VUV beam intercepts a volume containing 2% of the desorbed neutrals, while the UV POSTI intercepts only 0.2% of the desorbed neutrals from that same volume. This interception volume can be increased by using multiple pass optical schemes which will be discussed later. Moreover, one may be able to either use the VUV-POSTI laser to interrogate the same volume which was prepared by UV-POSTI. Other sequences involving multiple photon sources such as IR lasers, other excimer wavelength lasers, X-ray lasers, synchrotron light source which make available tunable radiation from visible to X-ray wavelengths and even high intensity photon lamps which can be mechanically or electrically chopped into a few tens of microseconds of pulse length can be applied. It is also apparent to one skilled in the art that any desorption source other than a UV laser can be used to liberate neutral elements or molecules from the surface. Especially useful are microfocused liquid metal ions or microfocused cluster ion sources which may be based on magnetron or ECR ionization processes. Other energetic particle beams such as electrons or fission fragments may have usefulness depending on the applications.

The technique of combining UV and VUV POSTI has been extended to protein standards in DHB. As in the case of angiotensin, the UV POSTI produced an intact protein signals which can be compared to the VUV POSTI fragmentation results. This capability has never been heretofore demonstrated.

The use of the three (or more) laser sequences in front of the ion mobility cell allows different types of information to be extracted simultaneously from the same spot on the surface where the surface is irradiated with a microprobe particle desorption source (e.g. UV MALDI laser). These sources are not restricted to lasers and may include focused ion beams cluster ion beams, and tunable photon sources among others. Likewise the post-ionization sources are not restricted to lasers either. Electrons, photons, metastable atoms or ions, chemical ionization sources (such as the ESI demonstrated by Vertes) may be combined within the ion-mobility cell and applied sequentially. Various sequences of these alternative post-ionization sources can be applied with the laser post-ionization sources already described.

When applied to tissue analysis, UV and VUV POSTI techniques yield complementary information for the lipids, peptides and proteins on the surface, and will also yield information about other biomolecules known to be on the tissue surface including drug molecules, glycolipids, glycoproteins, nucleic acids, bacterial lipids, to name a few. Moreover these techniques can be readily applied to other materials including synthetic polymers or particulate arrays on inorganic surfaces as well. Elemental analysis from surfaces can benefit strongly from the combination of the post and photo-ionization within the ion-mobility cell.

Spot profiles were obtained from rat brain using both DHB and AuNP matrices. The data indicate that the UV post-ionization produces a signal that is enhanced and unfragmented from tissues using both matrices. Interestingly, the VUV post-ionization spectra acquired from photo-fragmentation of intact tissue proteins yielded a complicated singly charged peptide spectra with a mass-to-charge ratio in excess of 30 kDa. Purification of proteins in real-time with ion mobility makes it possible to systematically study protein fragmentation under VUV irradiation. Thus, for the first time an ideal instrumental platform for determining the unknown VUV fragmentation pathways of large proteins and protein complexes is provided herein.

The low intensity of the UV post-ionization signal compared to VUV post ionization is explained by nearly one order of magnitude less fluence from the UV when compared to the fluence of the VUV laser. In other examples, UV lasers are capable of matching the VUV fluence over large areas and may be used in the three laser sequence. The "in source photo-fragments" seen using the VUV laser (right-most panel of FIG. 6) all match with structural photo-fragments known to come from the peptide.

Tissues prepared either with DHB or AuNP matrices show VUV photo-fragments 100 Da to greater than to 100 kDa. Spot profiles were obtained from rat brain tissue using both DHB and AuNP matrices. The spot profile data show that the UV-POSTI post-ionization produces enhanced and unfragmented low mass lipid and small molecule signals from tissues with both matrices just as was observed when studying the angiotensin standards. Interestingly, the VUV post-ionization spectra acquired from photo-fragmentation of intact tissue proteins yielded a complicated singly charged peptide and protein spectra with a mass-to-charge ratio in excess of 100 kDa. The data described above with the UV laser demonstrates the principle. In additional examples, a more powerful UV laser is used so that the fluence and flux is equal to that of the VUV laser. Moreover, multiple pass optical cavities can enhance the performance of this instrumentation The following example extends the results from angiotensin to a real tissue. Ion mobility MS/MS with vacuum ultraviolet (VUV) photo-fragmentation may allow de novo sequencing and top down real-time identification of peptides and proteins, lipids, and glycolipids.

Figure 7:
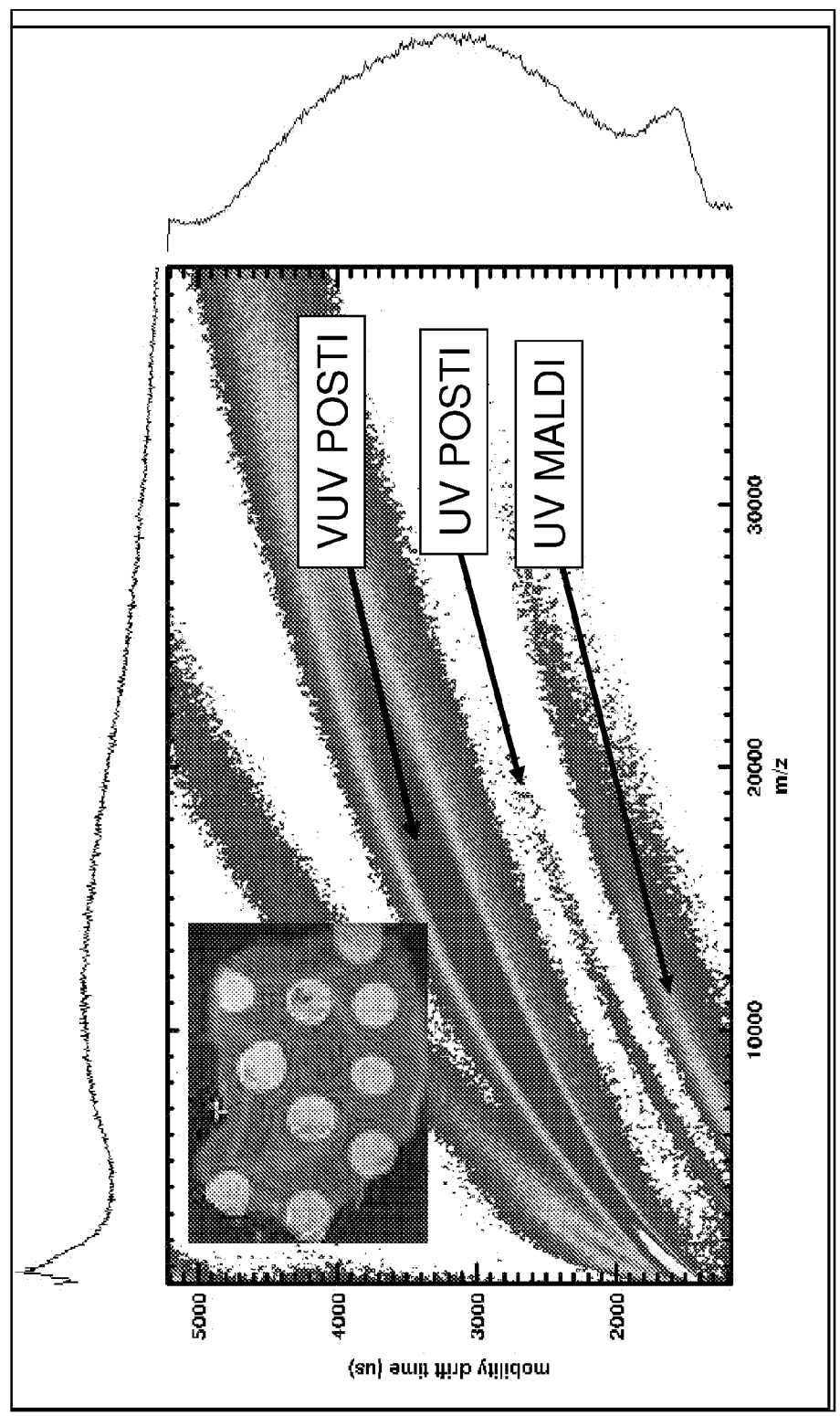
FIG. 7 shows an IM-oTOFMS spectrum of the ion mobility drift time versus the mass-to-charge ratio for a rat brain tissue sample covered with dihydroxybenzoic acid (DHB) matrix.

The data in FIG. 7 shows data from tissue spot profiles which were taken with three lasers UV MALDI, UV POSTI, and VUV POSTI. In FIG. 7, the post-ionization data from these tissues is analogous to the three laser data for angitotensin in FIG. 5. Tissues were prepared with DHB matrix (or Au) to demonstrate VUV photo-fragmentation of neutral proteins. These results have been confirmed this with pure Lysozyme standards—data not shown. The mass range of these VUV photo-activated (and fragmented) large protein ions extends to 100 kDa. Furthermore, spot profiles were obtained from rat brain using both DHB as well as AuNP matrices. The spot profile data show that the UV POSTI type post-ionization produces enhanced and unfragmented low mass lipid and small molecule signal from tissues with both matrices. Interestingly, the VUV POSTI type post-ionization spectra yields complicated singly charged peptide and protein spectra extending the mass-to-charge ratio (m/z) to over 100 kDa from photo-fragmentation of intact tissue proteins.

Using the UV post-ionization data in FIG. 7, the biologically driven ladder sequence of dynorphin A and B has been tentatively identified by measuring the mass-to-charge ratio alone. Ultimately, the mass-to-charge ratio of the biologically driven ladder sequence of dynorphin A and B culminates in the production of LeuEnkephalin at m/z 555. Heretofore, these peptides have not been possible to unambiguously measure with MALDI tissue spot profiling due to extensive cationization, as well as, isobaric interferences from lipids and matrix adducts.

Thus, UV post-ionization in combination with IM-oTOFMS is a powerful analytical technique for tissue analysis as demonstrated by the results for the three laser analysis of angiotensin. This three laser approach provides a top down and bottom up approach to analysis of a portion of a tissue surface, and offers an alternative to sequence analysis using micro deposition of enzymes which digest proteins in-situ on the surface. In fact, with more ion mobility and mass spectra resolution the entire "digest" of proteins and peptides for sequence analysis is done by photons. UV POSTI gives all the intact unfragmented peptides and proteins in the form of mostly H$^+$ adduct ions with a few alkali cations. When followed by VUV post-ionization, the VUV post-ionization gives the sequences. Refined bioinformatics tools can then sort all the sequences and all the parents with each other.

Giant fullerenes can be used as an ion mobility and mass spectroscopy internal calibration standard because the giant fullerenes can be separated from biological analyte ions by the ion mobility.

The utility of bioinformatics tools is tremendously enhanced by the demonstrated capability to incorporate fullerenes as internal standards which can give parts per million (ppm) or better mass accuracies for unknown ions. Especially giant fullerenes, when used as internal standards, provide ions of known structure with a known mass-to-charge ratio and ion mobility cross-section as seen in FIG. 5. These so-called giant fullerenes are akin to $C_{60}$ but are larger closed structures which have been considered worthless by-products of reactions which are designed to produce single wall nanotubes. These very stable giant fullerenes are synthesized easy to non-destructively desorb and to be susceptible to VUV photo-ionization in the same way as $C_{60}$. This is fundamentally different to the use of the multi-mer formation of from $C_{60}$ which occurs when a pure $C_{60}$ film is laser irradiated. The giant fullerenes are discrete molecules which can be ablated with reduced laser fluence. In fact, it is possible to use such low desorption laser fluences that no direct ions are desorbed, yet when a VUV POSTI laser is crossed into the neutral plume evolving from the surface, copious giant fullerene radical cations are produced by photoionzition by the fluorine (or other excimer wavelengths above about 6 eV). Thus, a batch of these giant fullerenes can be characterized by ion mobility and mass spectroscopy both for MALDI and for POSTI calibrations. This characterization may include a comparison to ultrahigh resolution Fourier Transform Mass Spectroscopy. Fourier Transform Mass Spectroscopy (FTMS) is capable of identifying substitution elements in the otherwise relatively pure giant fullerene carbon structure. For example, nitrogen and/or carbon may be substituted with oxygen, or vice versa. The ultrahigh resolution FTMS data may be used to compute very accurate centroid data for the isotopic envelopes of each of these giant fullerene ions (and their substitutional atom contaminants) which can then be used as a mass calibrant points even in the m/z range where the oTOFMS cannot achieve isotopic resolution. Thus, one can prepare a UV and VUV active standard with known weights and mobilities. These known standards can be used as calibrants for mass ranges up to several hundred kDA. By taking a large batch of these characterized giant fullerenes, standards can be distributed to a calibrate different types of ion mobility mass spectrometers. This will allow researchers to more easily compare their data.

Within one researchers data, the mass accuracy and stability of these data are tremendously increased by use of such an overidentified set of standards. This in turn significantly reduces the number of possible matches with existing data base structures. It also allows better inter-comparison of ion mobility-mass spectra from different instruments in different laboratories. Giant fullerenes (or other fullerenes) can be added to the samples by intimately mixing the powder with the solid sample or liquid sample as a slurry, a toluene solution, or a chloroform solution.

The chemistry of the giant fullerenes is unappreciated within the community of mass spectrometry researchers and ion mobility researchers. The giant fullerenes provide a very well defined ion mobility trend line which extends over a very large range of masses. The larger of these fullerenes (fullerenes above 2000 Da) are insoluble in most solvents, but can be laser ablated onto any test sample surface. In some cases, the test sample is a biotissue. The smaller fullerenes (fullerenes below about 2000 Da) can be solvent extracted and purified. This purified lower mass giant fullerene material can then laser ablated onto a sample analogously to manner in which the higher mass giant fullerenes are applied. Moreover, the lower mass portion of the giant fullerenes may be sublimed. Thus, a Knudsen evaporator or other evaporation source can be used to quantitatively control thin film evaporation of these lower mass giant fullerenes onto a test surface substrate. The thin film evaporation can be controlled even at the level of partial monolayer coverages. These partial monolayer coverages may be several square centimeter area surfaces such as would be the case if multiple tissue sections on a standard stainless steel MALDI sample plate are being treated with matrix. Moreover, the sidewalls of the fullerenes can be chemically derivatized to provide additional calibrant molecules. These chemically derivitized fullerenes move more slowly in the ion mobility cell than their isobaric (same m/z) underivatized fullerene counterparts. All of the fullerene calibrants described herein have an ionization potential of 7 eV and below. Therefore, any VUV photon exceeding this energy (e.g. 7.8 eV Flourine laser) or any absorption of multiple UV photons whose combined energies exceed this ionization potential can easily create radical cations from the neutral fullerenes which are co-desorbed along with neutral analytes. The co-desorbed radical cations produced from the neutral fullerenes create an independent second calibrant trend line. This second calibrant trend line is associated with the analyte ions produced by the post-ionizing laser (see FIG. 8) Examples of the advantages of combining these calibrants, along with post-ionization within MALDI-IM-oTOFMS are described in more detail within the following sections.

Improvement in mass accuracy for MALDI-IM-oTOFMS is possible through the use of an internal mass (and mobility) standards comprising giant fullerenes. The use of giant fullerenes will improve the mass analysis in other applications in high throughput mass spectrometry and will enable high mass accuracy in tissue imaging for the first time. High mass accuracy cannot be achieved with any existing MALDI imaging spectrometer because of mass calibration drift during the hours of acquisition time that is necessary for image acquisition.

Figure 8:
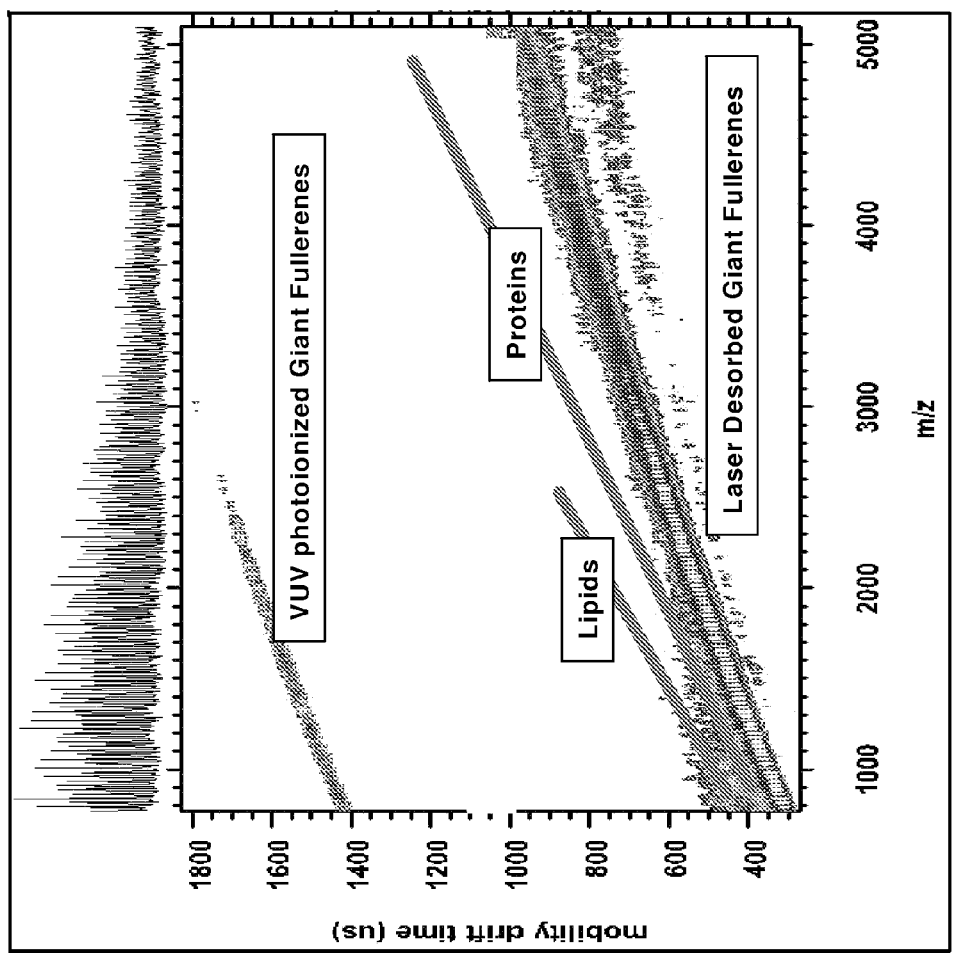
FIG. 8 shows a spectra derived from a mixture of derivatized and underivatized giant fullerenes that was pulsed with UV laser which gave desorbed giant fullerene ions with $C_2$ (carbon dimer) spacing extending up to a mass of around 20,000 Da.

FIG. 8 shows the very uniform distribution of ion intensities that are each separated by a mass-to-charge ratio of 24. This uniform distribution of ion intensities is a crucially useful feature and is produced because there are fairly uniform distributions of the giant fullerene molecules in the giant fullerene mixtures and the ionization cross-sections for these giant fullerenes are very similar. These mixtures may be used to test for any non-linearities in our mass calibration or used to establish the mass calibration of any other TOFMS over an unprecedented mass range. The derivatized mixtures of these giant fullerenes immediately qualify as an "external calibrant" which is used before and after the acquisition of spectra from unknown materials onto which unreacted giant fullerenes internal calibrants were also added.

If the spectra resulting from a whole cell lysate comprising post-ionized neutrals is too complicated, the resulting UV post-ionization ions can be sorted into multiple and sequential arrays of ion mobility cells. Once the ions are sorted into multiple and sequential arrays of ion mobility cells, the purified portions of the UV post-ionized ions can be sequentially photofragmented by exposing the ions to ionizing radiations, such as VUV.

In FIG. 8, the UV Laser Desorbed Giant fullerene ions extend with $C_2$ dimer spacing over the mass range up to in excess of 60,000 Da. Notice that the distribution of ions is very uniform throughout the displayed m/z range (see derived mass spectrum on top of figure). The VUV photo-ionized neutrals are radical cations produced by the 1100 microsecond delayed VUV pulse. Two black lines show the trend line positions where lipids and peptides would appear if they were included in this mixture (as measured previously in FIG. 4).

Figure 9:
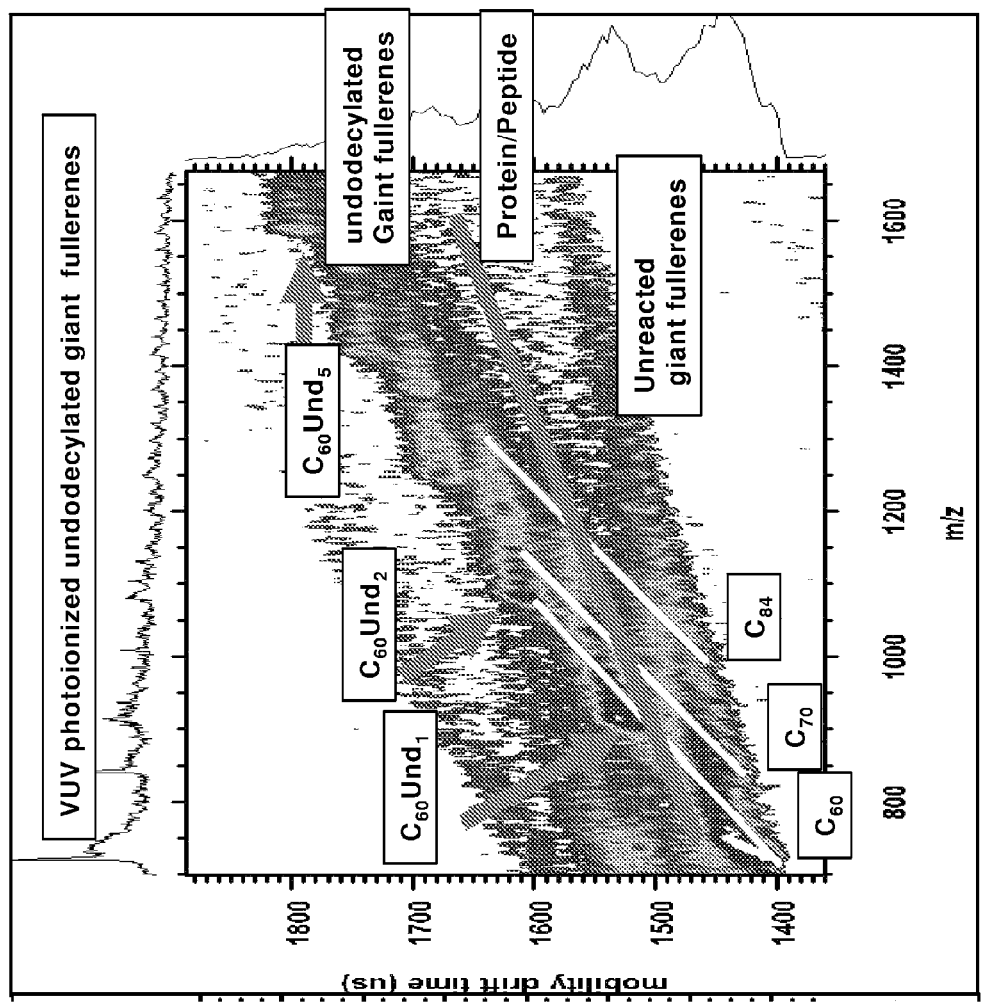
FIG. 9 shows a spectra with up to six undodecyl (Und=$C_{12}H_{25}$) groups chemically attached (preferentially) to the smaller (high radius of curvature) fullerenes such as $C_{60}$, $C_{70}$, and $C_{84}$.

FIG. 9 shows up to six undodecyl (Und=$C_{12}H_{25}$) groups are chemically attached (preferentially) to the smaller (high radius of curvature) fullerenes such as $C_{60}$, $C_{70}$, and $C_{84}$. The unreacted giant fullerene line and the undodecylated fullerene trend lines (white) extensively cover the drift regions of the low mass biomolecules (carbohydrates, lipids, peptides).

Also, external calibrants allow ion-mobility cross-section calibration using mixtures of sidewall reacted and unreacted fullerenes. A single mixture comprising both the undodecylated giant fullerenes and the unreacted giant fullerenes (shown in FIG. 9) can be used as an external calibrant prior to and after data acquisition of unknown biomolecular samples. This allows "bookending" the data set with an ion-mobility drift time and mass-to-charge ratio calibrant. Then, with the addition of an underivatized giant fullerene internal standard to the sample (or tissue surface) the stability of the instrument during any long term acquisition can be tracked and the stability (or lack thereof) can be validated by a repeat acquisition of the undodecylated calibration sample after the acquisition. To correct for any slight instrumental variations within the acquisition time, numerical routines will be written to recalibrate those time regimes in post-processing and perhaps also in real time.

The inclusion of known calibrants (such as cholesterol, phosphotidylcholine, and certain peptides and proteins) can be combined with the large fullerene nanoparticles. The use of these known calibrants which bracket the highest and lowest ion mobility velocities of the unknown molecular ions enables software to convert ion mobility drift velocities into accurate determination of the collision cross-sections. This depends on the accurate determination of the collision cross-sections of the calibrants. The collision cross-section is a characteristic of the molecule alone and should be independent of different types of ion mobility spectrometers which would be constructed in the future. The construction of this computational formalism can be tested against known (or measured) crossections of standard molecules which can then be inserted into a mixture with the calibrant as if they were unknowns.

Dynamically optimizing the oTOFMS operating parameters can allow collection and analysis of more than 50% of any of the ions of any mass which exit the ion mobility cell into the oTOFMS. In particular, the operating parameters to be optimized are the pulse extraction frequency and/or the energy of the ions entering the oTOFMS.

Presently, commercial oTOFMS instruments cannot achieve such high collection efficiency simultaneously over all mass ranges. This innovation is possible because the ion mobility separation always presents a moderately small mass range to the oTOFMS at any one ion mobility drift time. Also, this innovation is possible because the giant fullerene calibrant for attaining high mass accuracy by managing any small but significant nonlinearities associated with dynamic tuning schemes.

As explained in FIG. 10 through FIG. 16, the present disclosure provides a solution to why oTOFMS analyzers inefficiently collect ions above and below a certain mass range.

Figure 10:
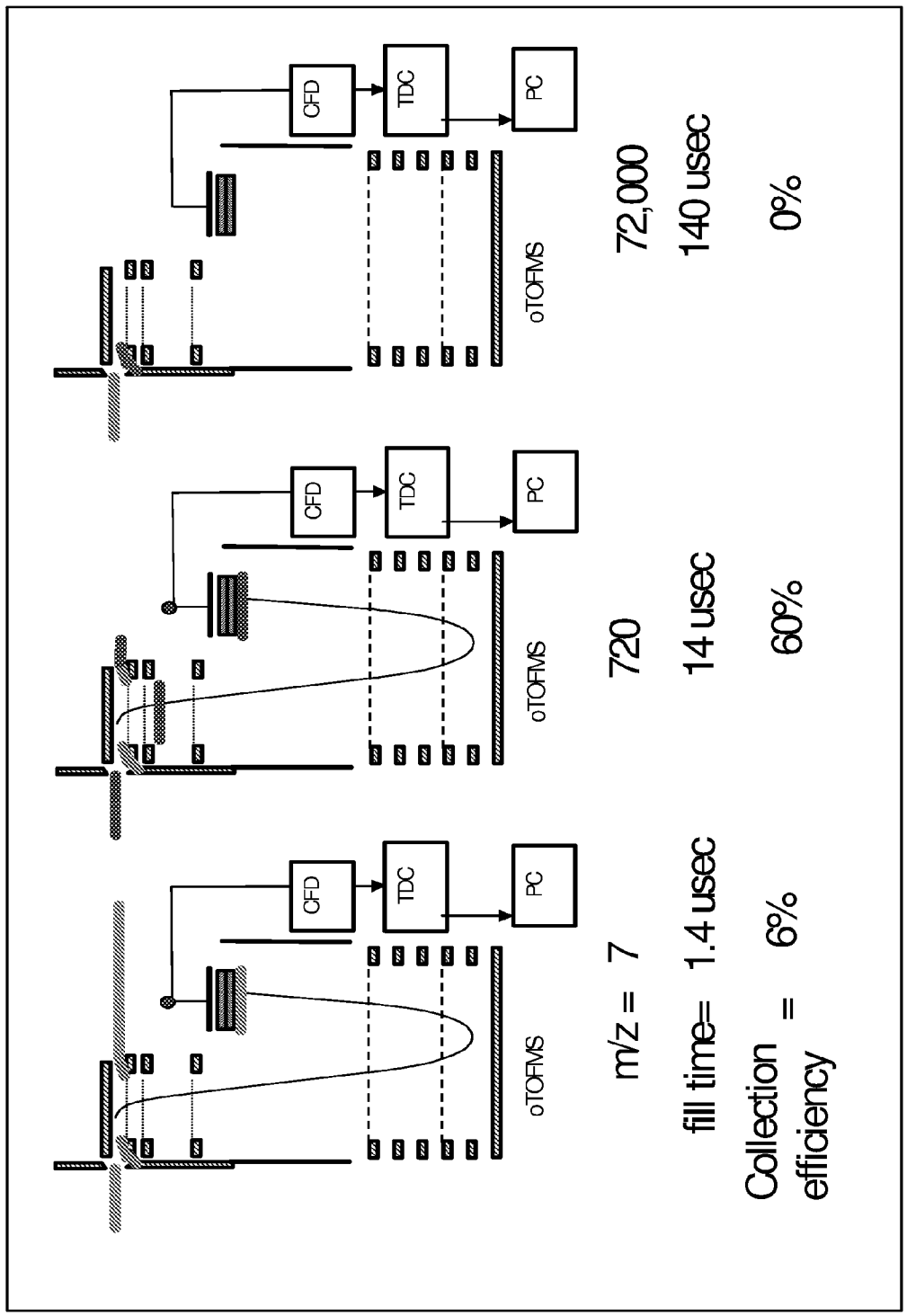
FIG. 10 shows an illustration of ion loss in an oTOFMS from a continuous source due to the difference in filling time of the orthogonal extractor as a function of mass.

FIG. 10 shows an illustration of ion loss from a continuous source due to the difference in filling time of the orthogonal extractor as a function of mass. All ion energies have energies of 20 eV when they enter the oTOFMS. The "fill times" are calculated for an extractor of 50 mm length. The flight time of $C_{60}$ once pulsed by the orthogonal extractor plates into the 0.5 meter long reflector is 25 microseconds. Thus, a pulsed extraction frequency of 40 kHz is ideal for $C_{60}$ but is too slow for a molecule with a mass of 7 atomic mass units and much too fast for structure with a mass of 72,000 atomic mass units (amu) which does not have time to get much farther than the entrance slit.

FIG. 10 shows three different mass ions, all cooled to the same energy and focused in a continuous stream into the oTOFMS extractor region. The fill time (the time necessary for a certain mass ion to completely fill the ortho extraction region) increases proportionally to the square root of the ions' m/z. Although the mass region around 720 can be collected with 60% efficiency using a pulsed extraction frequency of 40 kHz, the low and high mass ions are barely detected at all. Likewise, the large ions can be collected with 60% efficiency if the pulsed extraction frequency is lowered to 3.5 kHz which allows mass 72,000 amu to completely fill the extractor region after each extraction pulse. However, a mass of 720 amu would be collected with 6% efficiency and mass 7 amu would be almost totally lost. Since only a very few of these ions would be in the extractor during pulsing. Thus, it is necessary to optimize for high mass or low mass, but not both high and low masses simultaneously. The inability to optimize for both high and low masses is not acceptable. For example, when detecting proteins (a high mass species) it is necessary to efficiently measure the low mass elements including elemental ions as well.

Figure 11:
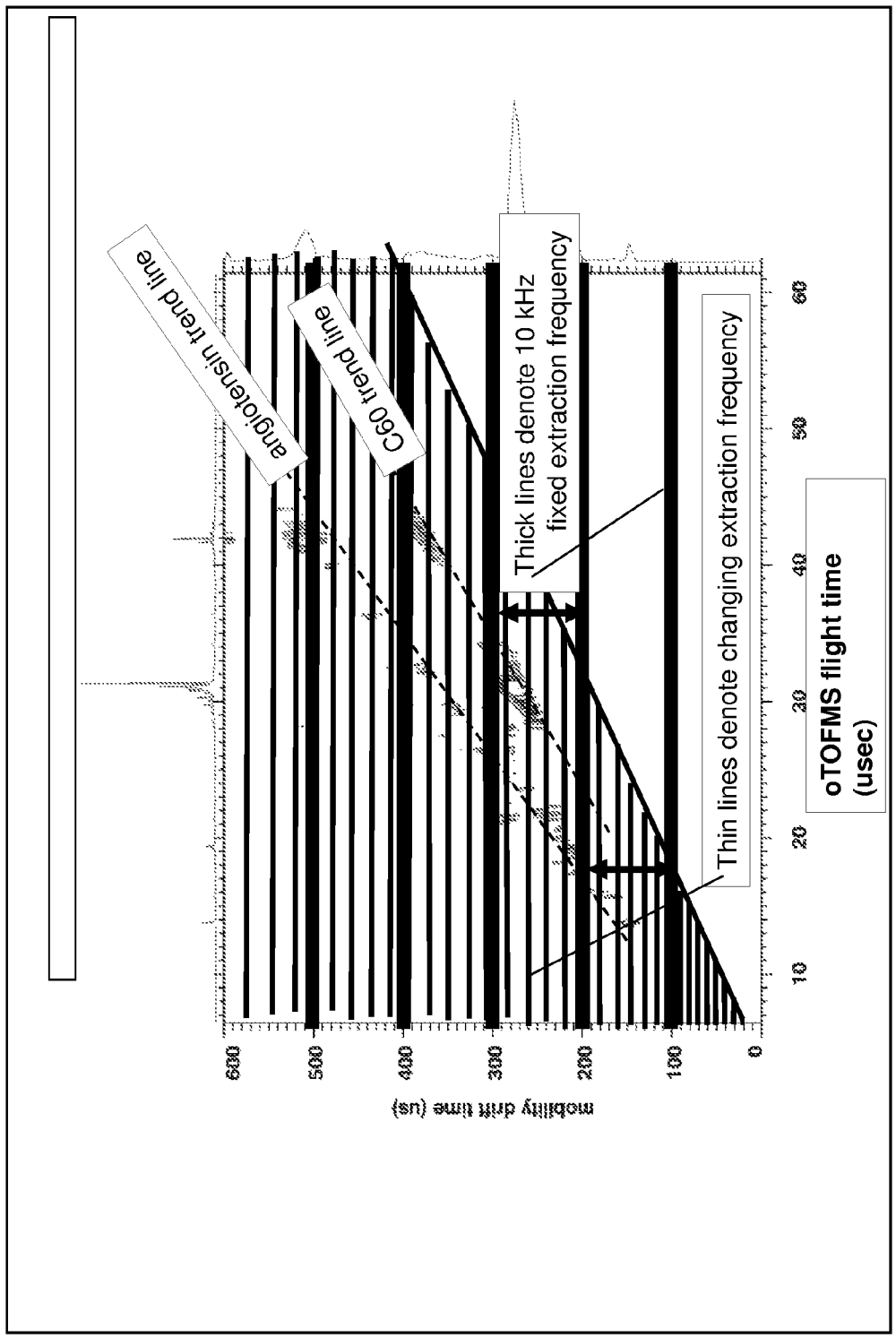
FIG. 11 shows a MALDI-IM-oTOFMS spectrum of $C_{60}$ and angiotension wherein the spectrum illustrates a fixed frequency when compared to the variable frequency produced by oTOFMS extraction.

The problem of the inability of the oTOFMS to measure both high mass species and low mass species is depicted in FIG. 11. Attention is directed to the evenly spaced horizontal lines at 100 μs, 200 μs, 300 μs, 400 μs, 500 μs, and 600 μs which represent time at which the extractor is pulsed. The 100 microsecond spacing (10 kHz extraction frequency) is necessary to optimize the oTOFMS for 60% detection of 10,000 amu; however, as can be seen, this throws away most of the signal in the low mass region. The thickness of the horizontal lines at 100 μs, 200 μs, 300 μs, 400 μs, 500 μs, and 600 μs intersects the small percentage of the ions on each trend line which would be detected at each of the extraction times. The remainder of the ions, located between the horizontal lines at 100 μs, 200 μs, 300 μs, 400 μs, 500 μs, and 600 μs lines, is lost. Nevertheless, this method of evenly spaced pulsing for the oTOFMS is commonly used since it minimizes many of the electronic instabilities that contribute to drift and mass inaccuracies.

As shown in FIG. 11, the MALDI-IM-oTOFMS spectrum of $C_{60}$ and angiotensin have a fixed frequency compared to variable frequency oTOFMS extraction. The horizontal lines at 100 μs, 200 μs, 300 μs, 400 μs, 500 μs, and 600 μs signify where extraction pulses are occurring at a frequency which optimally detects a mass-to-charge ratio equal to 10,000 amu. At this 10 kHz pulse rate most of the low mass ions are undetected. The width of the line approximates collection of only 5% of the ions in the low mass region and the remaining ions are lost. In contrast, the lines between horizontal lines at 100 μs, 200 μs, 300 μs, 400 μs, 500 μs, and 600 μs show the variation of orthogonal pulsed extraction frequency as a function of ion mobility drift time so that the large gaps of the 100 is sampling period are filled. Thus all ions along a trend line region can be collected with high efficiency.

As the mass of the ions which are eluting from the ion-mobility cell into the extraction region of the oTOFMS increases, it is well known in the prior art that increasing the energy of the ions and or decreasing the extraction frequency into the oTOFMS. An example of increasing the extraction frequency is shown in FIG. 11. In place of the evenly spaced ortho-extraction pulses (horizontal lines at 100 μs, 200 μs, 300 μs, 400 μs, 500 μs, and 600 μs), it is desirous to substitute a variable frequency extraction pulse sequence (thin lines between thick horizontal lines at 100 μs, 200 μs, 300 μs, 400 μs, 500 μs, and 600 μs). The pulse frequency is successively lowered as a function of drift time (more space between the thin lines) to allow maximum fill time of the ortho-extractor as the ions become heavier. It is possible to either adjust this frequency by matching it to the peptide trend line in which case all of the peptides and proteins would be acquired with about 60% efficiency. On the other hand, it is possible to tune the frequency to track the masses along an imaginary trend line between the peptides and fullerenes so that each group is detected with around 50% efficiency.

The implementation of the variable energy and or pulse frequency may seem straightforward, but there are many good reasons why researchers have avoided this. Most have to do with the substantial non-linearities which appear in the mass spectrum when these hardware and software changes are made during the time the ions are introduced to the extraction region of the oTOFMS. On the hardware side, introducing acceleration potentials to change the ion energy can change (desirably in fact) the beam profile entering the oTOFMS extractor, while in the process of varying the extraction frequency, significant voltage drift to a ground-based high voltage floated AC-coupled high voltage pulser for oTOFMS operation can occur. High voltage pulsers are often prone to pulse rate dependant drift. A variable rate extraction cycle complicates DC offset corrections necessary with this ground-based approach and it is necessary to use a floating pulser supply. In terms of software, non-linearities in the oTOFMS flight times may be introduced by the variable rate pulsing due to frequency and width dependent extraction pulse shapes. The use of the just described giant fullerene internal calibrants enables mass calibration corrections of oTOFMS data even in real time. These nonlinearities and their drastic effects on mass accuracy are often the reason that the approaches which change the energy or the extraction frequency are not more often used. Our use of the evenly distributed internal (and external) fullerene calibrants are the innovation which can make either of these approaches practical. For example, in FIG. 11, the angiotensin and the fullerene trend lines are seen to occupy different regions of the three dimensional IM, m/z and intensity space. Thus the peptide ions will always be lighter than the fullerene calibrants in any particular oTOFMS extraction pulse (which occur at an IM time represented by the horizontal lines). Therefore, many nonlinearity software correction which applies to the fullerene trend line may not be transferable to correct the peptide ion masses. This situation can be remedied by constructing look-up tables derived from experiments in which either the UV-MALDI or the UV-POSTI or the VUV-POSTI are used either separately or alone in a rapid sequence to provide multiple giant fullerene calibrant trend lines which are offset from each other by around 50 microseconds. In this way a controllable panoply of giant fullerenes will be present in any and all oTOFMS extraction pulses. The nonlinearity of the mass correction as a function of the change in the instrumental parameters including the changing of the ion energy or the decreasing of the pulsing frequency can then be corrected through look-up tables which are constructed from these data so that any mass at any IM drift time can be corrected. These look-up tables can be stored and updated in the FPGA or the host computer. Any drift in the stability of these calibration look-up tables during an actual experiment can be continuously verified by testing the internal and external giant fullerene calibrants which are incorporated onto or alongside the sample surface.

Another objective of the present invention is to eliminate storage of unused ion-mobility/mass-to-charge ratio space. In FIG. 11, the 2-dimensional mass-mobility space probed in the MALDI-IM-oTOFMS experiment is characterized by upward sloping 'trend lines' for peptides and fullerenes. Lighter mass ions arrive into the oTOFMS first and are extracted with an extraction period appropriate for the heaviest ion of interest, even though no heavier ions have exited the drift cell as yet. This drift time separation leads to an area of 2-dimensional space below and to the right of the 'trend lines' devoid of signal. Eliminating the pixels in this void area from storage is accomplished by decreasing the extractor pulse rate while simultaneously increasing the active acquisition time of a time to digital converter to include higher masses. As one proceeds up the trend line, the extractions become longer and longer. This scheme leads to a compression of ion mobility time sample bins for shorter drift times and mitigates the effects of low mass ion loss characterized by the fixed rate extraction cycles. However, there are hardware difficulties associated with introducing a variable rate extraction pulse cycle. These difficulties must be overcome to make this approach work. To overcome these difficulties a non-constant pulser AC-coupling offset may be introduced into the mass calibration, and/or a non-linearity may be introduced into the mass calibration.

Each of the proposed methods to improve ion yields, increase TOFMS collection efficiencies, and collect more precise mass and mobility information. However, each of the proposed methods carry an additional computational demands. Laser interleaving presents challenges to acquisition and control software. The laser trigger positioning relative to the extraction cycle must be known at all times and also adjusted in real-time for each MALDI laser firing. High laser repetition rates and high data event throughput combine to stress even modern computer operating systems. Pulsed oTOFMS extraction timing and especially variable rate extraction control require sophisticated timing generation platforms. In an effort to decouple the timing sequence control from data acquisition and processing demands, FPGA-based pulse sequence controller can be used to obtain complete timing sequence automation, independent of the host computer. This FPGA module has the ability to embed laser interleaving timing information and non linear calibration information into the data stream, removing the requirement for any real-time intervention of the data acquisition computer.

The time-to-digital (TDC) electronics currently in use has eight independent timing channels triggered from a common start signal with one connected to each anode. The number of TDC channels and the number of anodes can of course be desirably increased. The detection of a signal into eight position-sensitive channels has additional benefits related to instrument tuning and calibration. The software must acquire, display, and save all time-to-digital events and calibration corrections so that the complete experiments can be reconstructed in entirety at a later time if needed.

Figure 12:
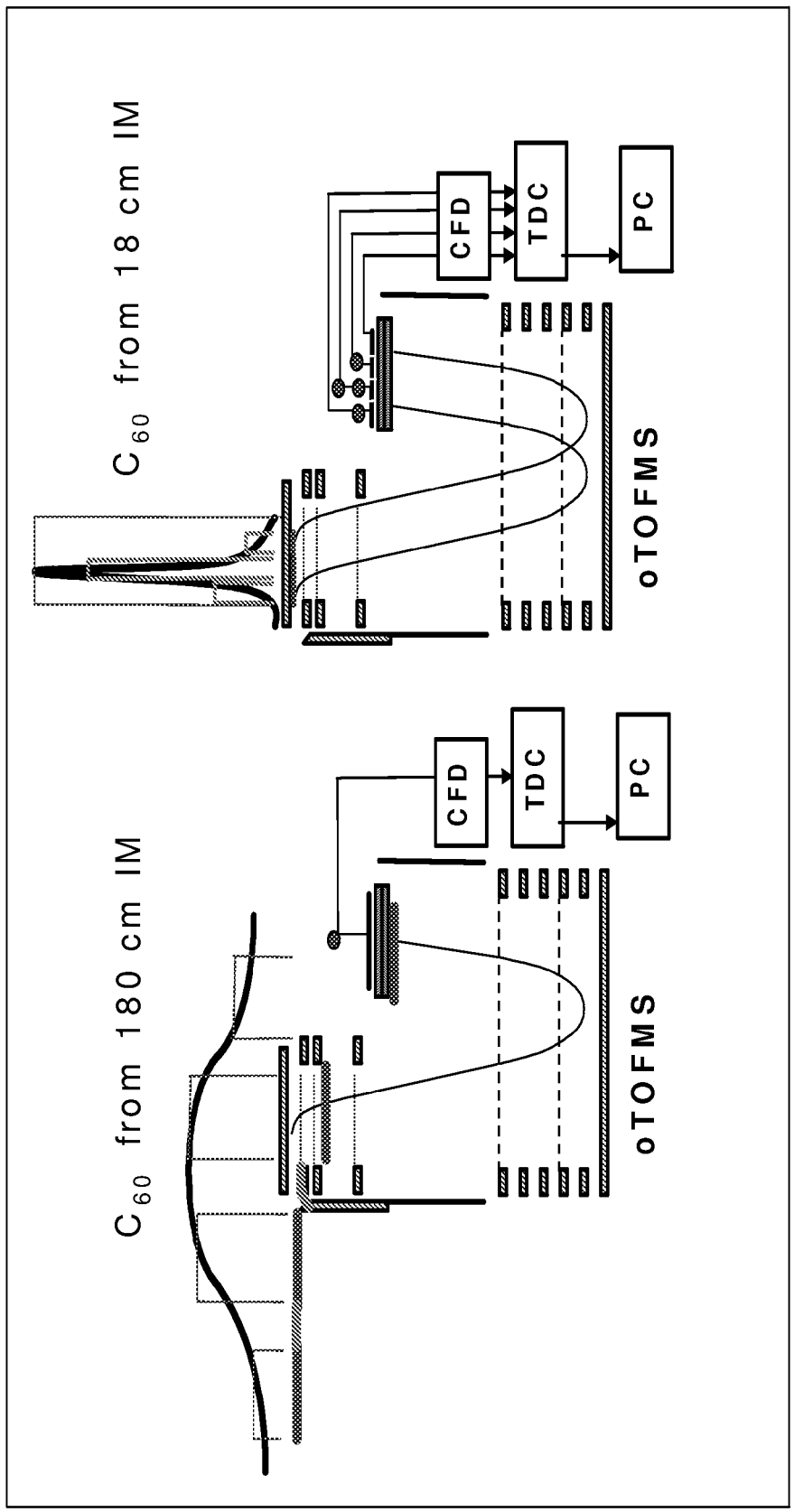
FIG. 12 shows a comparison of ion mobility peaks widths from a long ion-mobility cell compared to a short ion-mobility cell operating at the same resolution. The 50 microsecond wide peak from a 1.8 meter cell overfills the extraction plates while with the 5 microsecond wide peak from an 18 cm cell is completely contained within the extractions plates.

High resolution ion mobility spectra can be measured when the IM peak width is smaller than the extraction fill-time of the oTOFMS. FIG. 12 shows the comparison of the 50 microsecond wide peak from a 1.8 meter cell with the 5 microsecond wide peak from an 18 cm cell. The orthogonal extraction fill time is 14 microseconds in both cases.

Also, the schematic in FIG. 12 illustrates the problem to be solved. It is very desirable to make the ion-mobility cell as short as possible so that the ions can elute as rapidly as possible. A compelling reason for fast ion mobility cells is that imaging and other high throughput applications can be finished faster than with longer ion-mobility cells. The multianode detector must, therefore, shoulder the burden of retaining the high resolution of the ion-mobility since the peaks of 5 microseconds (in the example in FIG. 12 and the data of FIG. 13) is three times less than the total fill time of the orthogonal-extractor. The multianode retains the ion-mobility resolution by mapping the ion elution position with the orthogonal extractor onto specific anodes in the multianode. These eight anodes (four in FIG. 12 for simplicity) subdivide the 14 microseconds orthogonal extractor fill time for $C_{60}$ into an ion-mobility drift time with better than 2 microseconds drift time resolution. Data showing what happens to the resolution when a multianode is not in place are seen in FIG. 13.

Figure 13:
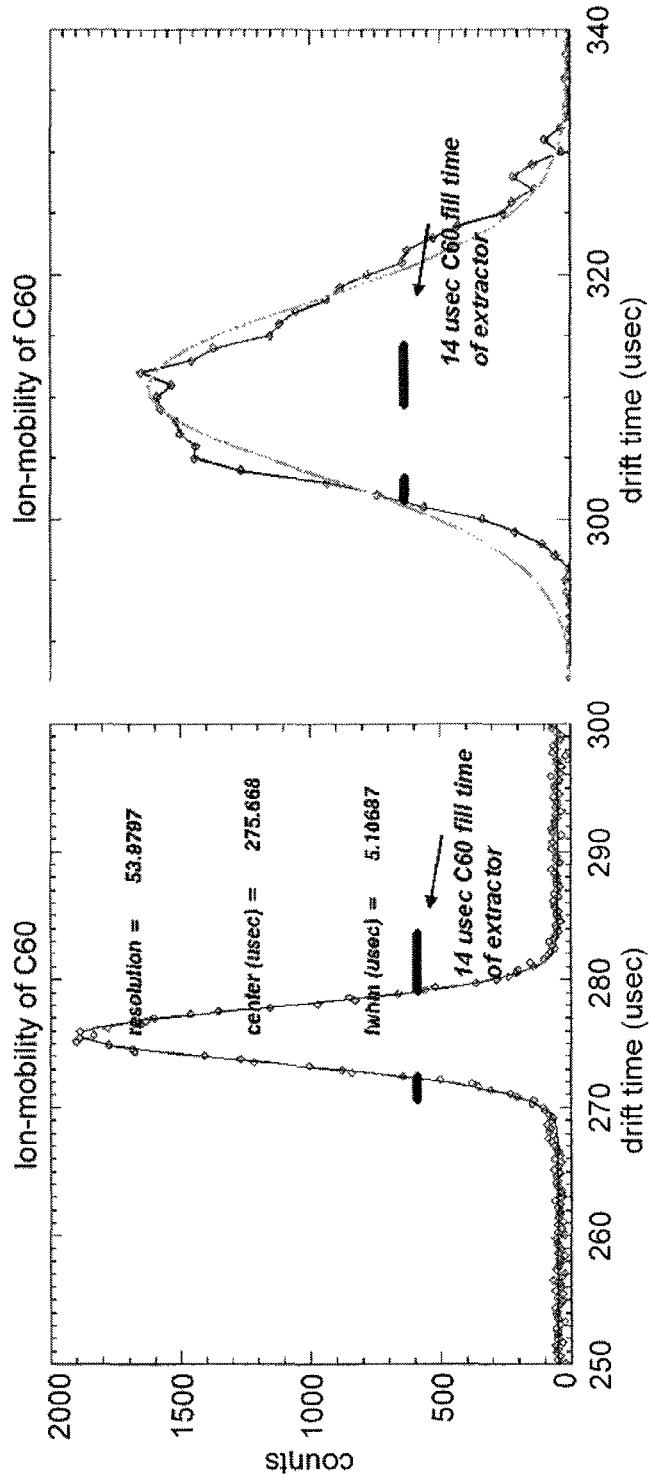
FIG. 13 shows a comparison of the ion-mobility resolution measured with an in-line detector (left panel) and ion-mobility resolution obtained with an oTOFMS (right panel)

FIG. 13 shows a comparison of the ion-mobility resolution measured with an in-line detector (left panel) and resolution obtained with oTOFMS (right panel). Ions exit the ion-mobility drift cell interface with an energy of approximately 23 eV and retain this energy after passing through ion-optics into the pulse extraction region of the orthogonal time-of-flight (oTOFMS) mass spectrometer (as shown in FIG. 1). The extraction/detection plate active area in the current oTOFMS design is 3.5 cm in length resulting in a velocity for $C_{60}$ (M/Z=720) of 2.5 mm/μsec and an extraction plate transit time of 13.7 μusec. Currently, an ion-mobility cell can produce resolutions in excess of 50 for $C_{60}$. The ion "packet width" entering the extraction plates is approximately 5 μs. FIG. 14A shows one such 50 resolution ion-mobility spectrum for $C_{60}$ ions obtained with an in-line Multichannel plate detector (MCP) placed at the location of the oTOFMS extraction plates.

Figure 14:
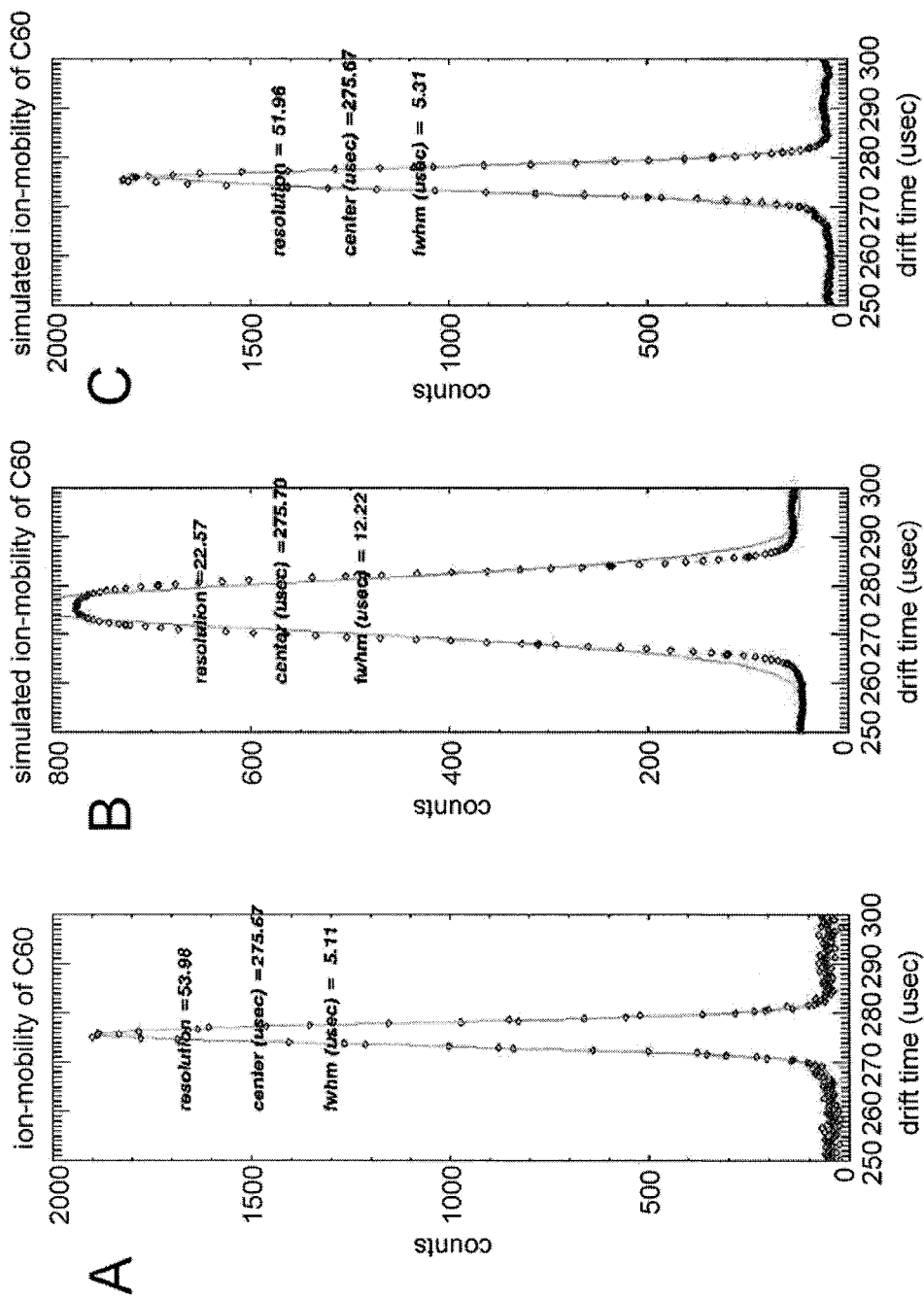
FIG. 14 shows a comparison of the MALDI ion-mobility profile of $C_{60}$ (FIG. 14A), simulated MALDI ion-mobility profile of $C_{60}$ (FIG. 14B), and a simulated MALDI ion-mobility profile that was measured on the individual anode elements of a multi-anode detector (FIG. 14C).

FIG. 14 shows the ion-mobility and the simulated ion-mobility of $C_{60}$. FIG. 14A shows a MALDI Ion-Mobility profile of $C_{60}$ in an 18 cm drift cell in 7 Torr helium with an ion-mobility resolution 54. FIG. 14B shows a simulated MALDI Ion-Mobility profile of $C_{60}$ after convolution of a 5 microsecond wide ion-mobility peak in FIG. 14A with the 14 microsecond fill time (ion transit time for $C_{60}$) into the time-of-flight extraction plates. The blue circles represent 2 microsecond sampling of the curve with the Gaussian fit parameters in black. FIG. 14C shows a simulated MALDI Ion-Mobility profile of measured ion-mobility peak what was measured with individual anode elements of a multi-anode detector. The intrinsic ion-mobility resolution is correctly recovered even when the detector transit times are less than the ion packet width being measured.

If, instead of an "in-line" ion detector, the ions pass into the extraction plates of the oTOFMS. Also, the 5 μs ion packet width is convoluted with a square-wave function whose width is equal to the 13 μs transit time of $C_{60}$ through the plates. If the signal obtained in FIG. 14B is convoluted with the extractor width function, the peak is broadened as shown in FIG. 15B. The ion-mobility drift time is sampled in the 2-dimensional IM-oTOFMS experiment on a much coarser scale than the data sampling shown in FIG. 14 and the blue circles in FIG. 14 are the interpolated 2 μs sampling intervals. Fitting the blue circles to a Gaussian profile gives the expected decrease in the measured ion-mobility resolution in to the 20 range.

If the spectra corresponding to a whole cell lysate which contains all post-ionized neutrals is too complicated, the ions resulting from the UV post-ionization can be sorted into multiple and sequential arrays of ion mobility cells. Then, the purified portions of the UV POSTI ions can be photofragmented sequentially by further ionizing radiations such as VUV.

Figure 15:
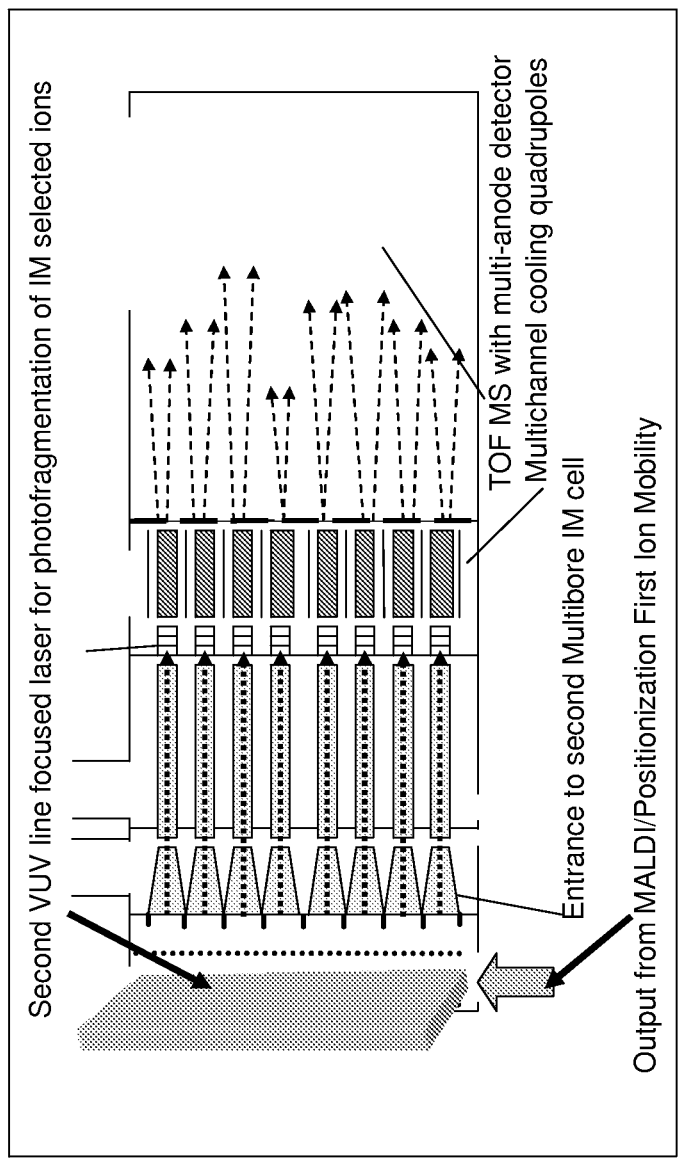
FIG. 15 shows a second ion-mobility array for performing tandem IM-IM-oTOFMS separation of molecules desorbed into a first ion-mobility cell from a tissue surface.

FIG. 15 shows a second ion-mobility array which allows tandem IM-IM-oTOFMS separation of molecules desorbed into first ion-mobility cell from a tissue surface. It is possible to construct an opposing array of ion mobility cells going into a second oTOFMS spectrometer which is biased to detect negative ions. Thus, when the second VUV-fragmentation or post-ionization laser is fired into a zwitterion, the positive and negative fragments will go simultaneously in opposite directions. If the transmission and detection of the IM-oTOFMS is high, then there is a good chance that the two structural ions would be detected in co-incidence thus giving the weight of the larger intact parent zwitterions by addition of the weights of the positive and negative fragments.

Figure 16:
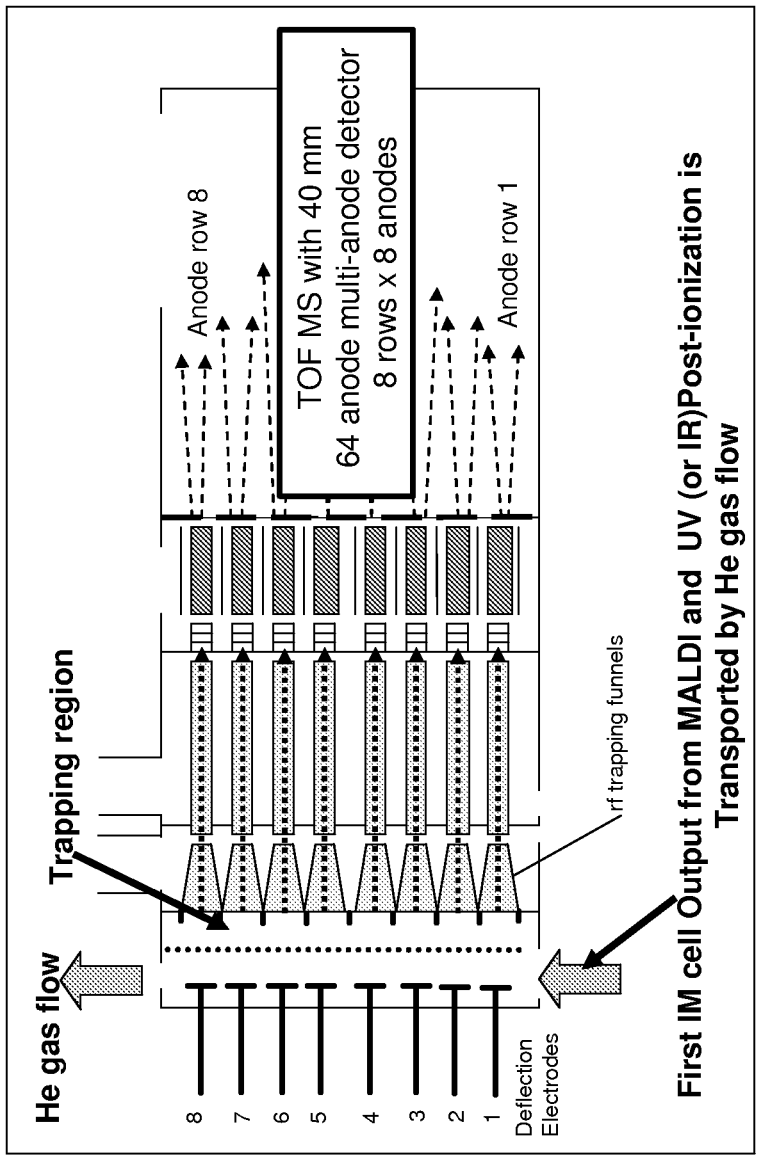
FIG. 16 shows an ion-mobility array which allows purification and trapping of ion-mobility selected ions prior to fragmentation.

FIG. 16 shows an ion-mobility array which allows for the purification and the trapping of ion-mobility selected ions prior to fragmentation. The configuration shown in FIG. 16 is useful for VUV photo-fragmentation. This device operates with individual deflection electrodes which route ions into individual ion-mobility channels. When electrode 1 is biased, then all the ions entering from the first ion-mobility cell pass into channel 1 and onward to be analyzed by anode row 1 in the TOFMS (in this mode all ions pass from the first ion-mobility cell and through the channel 1 of the multi-ion-mobility array and into the mass spectrometer). However, if certain ions need to be photo-fragmented, then electrode 1 goes to ground and electrode 2 is biased to select ions of a certain ion-mobility drift time as the ions elute from the cell by deflecting these ions into trapping region 2. These ions are stored in the region 2 RF trapping until the photofragmentation is applied. During this storing time, the ions are balanced against a gas counter-flow and restraining electric fields. The ion-mobility resolution should improve to several hundred because the ions are traversing a much longer ion-mobility cell. The ion-mobility cell is longer because the gas moves over the ions instead of the ions moving through the gas. The process can be repeated through the remaining six channels so that up to seven ion-mobility resolved ions can be stored at any one time and further purified by the gas counter-flow. After slicing out the ion of interest, deflection electrode 1 is re-energized and the remaining longer drift time ions which are beginning to elute out of the first ion-mobility cell are deflected into the first ion-mobility channel and arrive at the detector along the anode row 1 as before. The detector is arranged so that each of the eight anodes collects eight independent IM-oTOFMS spectra. This makes it as though eight individual oTOFMS are working in parallel. Moreover, the trapping times can be made a few hundred microseconds long so that once the fragmentation of the ion-mobility selected ion occurs and the trap is emptied, then the trap can be refilled with another different type ion of interest and the fragmentation process repeated. This results in an mobility oTOFMS spectrum of the fragmented second ion type of interest being offset from mobility oTOFMS spectrum of the fragments from first ion type. The offset time is the time between the VUV fragmentation pulses. Using this ion-mobility channel overloading technique allows many more than 7 ions of interest to be simultaneously stored and photo-fragmented—all from one desorption laser shot.

Optical multi-passing of lasers through more of the unused neutral plume volume may increases ion yields from UV and VUV Post-ionization. This is accomplished by using a high-power Grin (Graded Refractive Index) Injection Herriot Optical Cavity.

Figure 17:
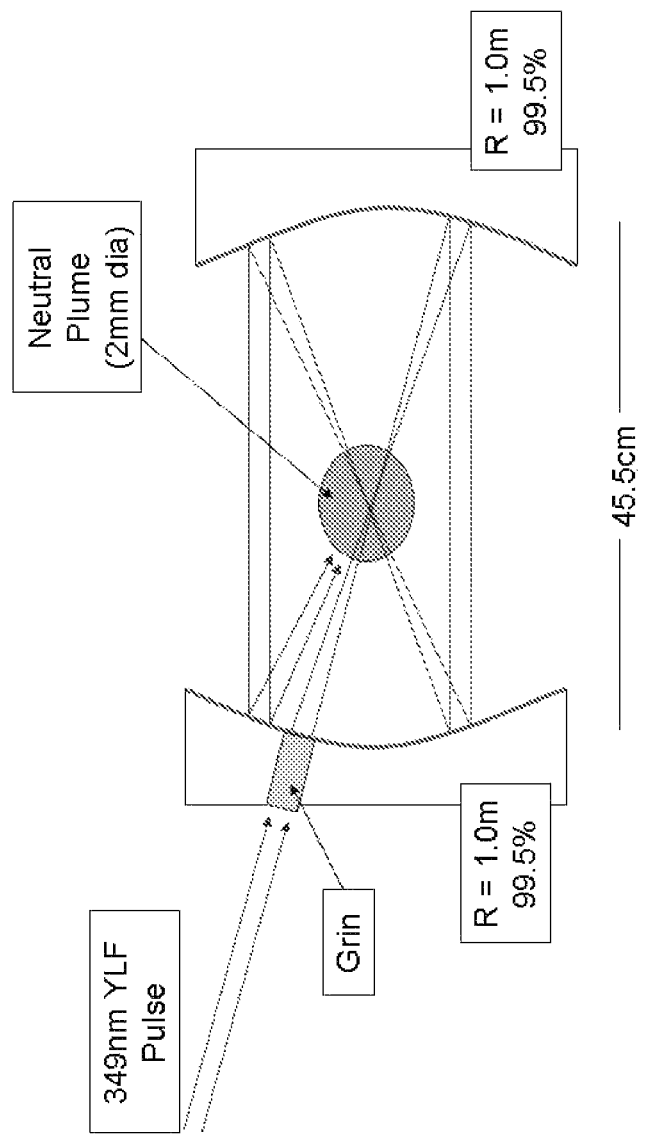
FIG. 17 shows a grin-injection multipass laser cavity for increasing the production of ions from neutrals by laser post-ionization.

A novel grin-injection laser cavity is shown in FIG. 17. Using commercially available grins, and custom coated minor blanks (also commercially available), a grin may be inserted into the input coupling minor of a stable near concentric optical cavity. This will allow for the maximum light coupling and retention of post-ionizing light within a given MALDI plume. In the FIG. 17, a general schematic is shown.

Injection of laser light into the Herriot cell is done through a commercially available grin lens. YLF, 349 nm, Q-switched laser light will enter, and be focused into the center of the cavity which has been placed over the neutral plume from the MALDI laser. The MALDI laser enters in out of the plane. Once focused into the neutral plume, the remaining light is re-collimated, and then re-focused after two bounces within the optical cavity. This allows for multiple passes of laser light at high fluences to be used out of one laser pulse. A semi-concentric optical cavity design is chosen to continually re-focus the laser into and out of the neutral plume.

The estimated beam spot size is around 70 µm at the focus, and will vary slightly as traversing the optical cavity. The multiple passes should be confined to pass through a 200 µm of volume which is needed for retention of ion-mobility resolution of more than 100. Using standard cavity ring down equations, it's estimated that the ringing of light within the cavity will be around 303 ns. This will provide an overall path-length of 91 m. Only half of the passes are focused so this provides an overall 100 passes of focused light through the neutral plume. This should in principle yield an enhancement of between 10 and 20 compared to only one pass of the post-ionizing laser through the neutral plume.

Furthermore, because the ring down event is complete within 300 ns, a 10 kHz laser for example, could be used to acquire spectra every 100 microseconds so that most of the evolving plume would be sampled with high mobility resolution. Thus, a series of spectra of approximately 10 UV post-ionization IM-oTOFMS spectra could be acquired after each UV-MALDI ion desorption pulse. Each of these spectra are offset from the other by 100 microseconds.

The application of such multiple pass optics can be applied also to the photo-fragmentation regions shown in FIG. 15 and FIG. 16. Thus, the multi-pass optics will find use both for creating ions from neutrals in the source region as well as in fragmenting the highly purified $MH^+$ ions for sequence analysis between the ion-mobility cells. This configuration may become useful for top down sequencing proteins especially when the resolution of the ion mobility cell and oTOFMS is improved.

The use of the multiple laser sequences between the surface and the entrance of the mobility cell can be extended. These multiple laser sequences can be used either before or the region after the ion output from the first ion-mobility cell but before the ions enter the second. These regions can also benefit from including newly emerging electron capture dissociation devices which can readily be used in combination with the photo-fragmentation techniques. Positioning the multiple laser sequence in the region between two ion mobility cells allows for the purification of the molecule of interest in the first ion mobility cell followed by photofragmentation and further purification by the second ion mobility cell.

The combinations of other desorption and post-ionization sources within an ion mobility cell followed by an ion mobility cell and mass spectrometer, or the use of the post-ionizing and fragmentation sources between the ion mobility cells or between the last IM cell and the oTOFMS are applicable as well. Use of other types of desorption probes such as cluster ions, DESI droplets (a type of cluster ion), Electrospray droplets. SIMS probes of all types including elemental or cluster ions or fast neutral elemental or cluster particles, X-rays and X-ray lasers, tunable light sources such as synchrotrons and electrons or high energy radiation sources for desorption. These same desorption sources may be used in any combination also for post-ionization or fragmentation as well—with our without their combination with lasers. A particularly potent "on demand" fragmentation combination would be the photofragmentation with VUV lasers coupled with a recent innovation in ECD (electron capture dissociation) by Barofsky at Oregon State University. This approach to ECD provides rapidly switched highly confined low energy electrons which upon attaching to multiply charged peptide ions yield "golden complement sequence peptides" to the sequences normally seen in CID and also VUV photo-fragmentation. Unambiguous identification of unknown peptides are thus quickly possible. Although all three of these fragmentation techniques can be combined, the combination of ECD and VUV is particularly potent because these are both available on demand within a few nanoseconds and can be coupled effectively together anywhere within or after the IM cell to produce multiple $(MS)^n$ identifications all within the time scale of the IM separations.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An apparatus comprising:
    an ion source for repetitively or continuously generating ions and neutrals;
    a post-ionization device fluidly coupled to said ion source to post-ionize or fragment at least a fraction of said ions and neutrals;
    an ion mobility cell capable of receiving the directly desorbed ions and the post-ionized ions;
    an ion extractor, fluidly coupled to said ion-mobility device capable of extracting said ions;
    a mass spectrometer fluidly coupled to and accepting said ions and fragment ions from said ion extractor,
    a position sensitive ion detector fluidly coupled to said time-of-flight mass spectrometer to detect said ions and fragment ions;
    a timing controller in electronic communication with said ion source and said ion extractor said timing controller tracking and controlling the time of activation of said ion source and controlling the activation of the post-ionization device and activation of said ion extractor according to a predetermined sequence to extract an analyte and a calibrant from a sample, wherein said calibrant is a giant fullerene or a derivatized giant fullerene; and,
    a data processing unit for analyzing and presenting data said data processing unit in electronic communication with said ion source, said ion extractor, and said position sensitive ion detector.

2. The apparatus of claim 1, wherein the ion post-ionization device is positioned to ionize and/or fragment ions at a location between the ion source and the ion mobility cell.

3. The apparatus of claim 2, wherein said post-ionization device is positioned before the ion extractor and is a photo-fragmentation device.

4. The apparatus of claim 1, wherein said timing controller or said data processing unit or both are in electronic communication with said post-ionization device.

5. The apparatus of claim 1, further comprising a multiple pixel ion detector positioned within the mass spectrometer.

6. A method for the collection of mass spectrometric data from a sample, comprising the steps of:
    desorbing a chemical species from said sample which produces a desorbed plume comprising a neutral species and an ionized species, wherein said sample comprises an analyte and a calibrant and wherein said calibrant is a giant fullerene or a derivatized giant fullerene;
    post-ionizing the neutral species generated in the desorbing step thereby creating a post-ionized species;
    separating the post-ionized species in a drift tube by ion mobility; and,
    further separating the chemical species in a mass spectrometer.

7. The method of claim 6, further comprising the step of adding matrix to the sample with a component selected from the group consisting of an inorganic cluster ion beam, a vapor deposition system, a desorption deposition source, and any combination thereof.

8. The method of claim 6, where the step of desorbing a chemical species is performed with an energetic particle.

9. The method of claim 6, wherein the step of desorbing a chemical species is performed by pulsing a source selected from the group consisting of a UV MALDI laser, an excimer laser, and IR laser, a cluster ion beam, and a tunable photon source.

10. The method of claim 6, wherein the post-ionization step is provided by at least one post-ionization source selected from the group consisting of a UV post-ionization laser, an excimer post-ionization laser, an IR post-ionization laser, a VUV post-ionization laser and a tunable photon source.

11. The method of claim 10, wherein the post-ionization source is pulsed with a time delay in relation to the pulsing of the source of the desorbing step.

12. The method of claim 6, wherein the calibrant is an internal calibrant or an external calibrant.

13. The method of claim 6, further comprising the step of filling an extraction region simultaneously with analyte and calibrant.

14. The method of claim 13, wherein the step of filling an extraction region further comprising the step of varying the sample energy and/or varying the extraction frequency as a function of ion-mobility drift time.

15. The method of claim 13, further comprising the step of extracting the analyte and calibrant.

16. The method of claim 15, further comprising the step of measuring the mass and time-of-flight of the calibrant and measuring the time-of-flight of the analyte.

17. The method of claim 16, further comprising the steps of comparing the time-of-flight of the calibrant and the time-of-flight of the analyte and detecting any non-linearities observed in the comparing step.

18. The method of claim 17, further comprising the steps of correcting for any non-linearities observed in the comparing step and determining the mass of the analyte by comparing the time-of-flight of the analyte with the time-of-flight with the calibrant.

19. The method of claim 6, wherein said sample comprises a MALDI matrix.

20. The method of claim 19, wherein said MALDI matrix comprises an organic acid.

21. The method of claim 20, wherein said MALDI matrix comprises a nanoparticulate matrix.

* * * * *